US011535888B2

(12) United States Patent
Kirino et al.

(10) Patent No.: US 11,535,888 B2
(45) Date of Patent: Dec. 27, 2022

(54) DUMBBELL-PCR: A METHOD TO QUANTIFY SPECIFIC SMALL RNA VARIANTS WITH A SINGLE NUCLEOTIDE RESOLUTION AT TERMINAL SEQUENCES

(71) Applicant: THOMAS JEFFERSON UNIVERSITY, Philadelphia, PA (US)

(72) Inventors: Yohei Kirino, Bryn Mawr, PA (US); Shozo Honda, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 192 days.

(21) Appl. No.: 15/754,194

(22) PCT Filed: Aug. 22, 2016

(86) PCT No.: PCT/US2016/048075
§ 371 (c)(1),
(2) Date: Feb. 21, 2018

(87) PCT Pub. No.: WO2017/035090
PCT Pub. Date: Mar. 2, 2017

(65) Prior Publication Data
US 2018/0251830 A1 Sep. 6, 2018

Related U.S. Application Data

(60) Provisional application No. 62/208,183, filed on Aug. 21, 2015.

(51) Int. Cl.
*C12Q 1/6853* (2018.01)
*C12Q 1/6851* (2018.01)
*C12Q 1/6811* (2018.01)

(52) U.S. Cl.
CPC .......... *C12Q 1/6853* (2013.01); *C12Q 1/6811* (2013.01); *C12Q 1/6851* (2013.01);
(Continued)

(58) Field of Classification Search
CPC ................ C12Q 1/6853; C12Q 1/6851; C12Q 2600/178; C12Q 2525/197;
(Continued)

(56) References Cited

U.S. PATENT DOCUMENTS

2010/0279305 A1 11/2010 Kuersten
2013/0011840 A1 1/2013 Chen et al.

FOREIGN PATENT DOCUMENTS

WO WO-2014071322 A1 * 5/2014 ........... C12Q 1/6853

OTHER PUBLICATIONS

Nichols et al. Current Protocols in Molecular Biology 2008; Chapters, Unit 3.15, pp. 3.15.1-3.15.4 (Year: 2008).*
(Continued)

*Primary Examiner* — Angela M. Bertagna
(74) *Attorney, Agent, or Firm* — Cozen O'Connor

(57) ABSTRACT

A method for specifically and efficiently quantifying the expression of targeted RNA variants with specific terminal sequences suitable to identify multiple isoforms bearing complex heterogeneity in terminal sequences by hybridizing a 5'-Dbs-adapter to the 5'-end of target RNAs, wherein the 5'-Dbs-adapter has a stem-loop structure whose protruding 5'-end base-pairs with the 5'-end of target RNAs, and wherein the loop region of 5'-Dbs-adapter contains a base-lacking spacer which will terminate reverse transcription in a subsequent step; hybridizing a 3'Db-adapter to the 3'-end of target RNAs, wherein the 3'-Db-adapter has a stem-loop structure whose protruding 3'-end base-pairs with the 3'-end of target RNAs; ligating both adapters with target RNAs by RNl2 ligation to form a "dumbbell-like" structure; and, amplifying and quantifying the ligation product by RT-PCR.

11 Claims, 27 Drawing Sheets

Specification includes a Sequence Listing.

(52) U.S. Cl.
CPC .. *C12Q 2521/107* (2013.01); *C12Q 2521/501* (2013.01); *C12Q 2525/121* (2013.01); *C12Q 2525/191* (2013.01); *C12Q 2525/197* (2013.01); *C12Q 2525/301* (2013.01); *C12Q 2525/307* (2013.01); *C12Q 2531/113* (2013.01); *C12Q 2561/101* (2013.01); *C12Q 2600/178* (2013.01)

(58) Field of Classification Search
CPC ........ C12Q 2525/121; C12Q 2521/107; C12Q 2521/501; C12Q 2525/191; C12Q 2525/301; C12Q 2525/307; C12Q 2531/113; C12Q 2561/101
See application file for complete search history.

(56) References Cited

OTHER PUBLICATIONS

Somel, M., et al., "MicroRNA, mRNA, and protein expression link development and aging in human and macaque brain", Genome Research, vol. 20, pp. 1207-1218, 2010.
Starega-Roslan, J., et al., "Structural basis of microRNA length variety", Nucleic Acids Research, vol. 39, No. 1, pp. 257-268, 2011.
Takeda, A., "The mechanism selecting the guide strand from small RNA duplexes is different among argonaute proteins", Plant & Cell Physiology, vol. 49, No. 4, pp. 493-500, 2008.
Tan, G.C., et al., "5' isomiR variation is of functional and evolutionary importance", Nucleic Acids Research, vol. 42, No. 14, pp. 9424-9435, 2014.
Zuker, M., "Mfold web server for nucleic acid folding and hybridization prediction", Nucleic Acids Research, vol. 31, No. 13, pp. 3406-3415, 2003.
Azuma-Mukai, A., et al., "Characterization of endogenous human Argonautes and their miRNA partners in RNA silencing", Proceedings of the National Academy of Sciences of the United States of America, vol. 105, pp. 7964-7969, 2008.
Bartel, D.P., "MicroRNAs: target recognition and regulatory functions", Cell, vol. 136, pp. 215-233, 2009.
Bizuayehu, T.T., et al., "Differential expression patterns of conserved miRNAs and isomiRs during Atlantic halibut development", BMC Genomics, vol. 13, No. 11, 14 pages, 2012.
Blow, M.J., et al., "RNA editing of human microRNAs", Genome Biology, vol. 7, R27, 2006.
Boele, J., et al., "PAPD5-mediated 3' adenylation and subsequent degradation of miR-21 is disrupted in proliferative disease", Proceedings of the National Academy of Sciences of the United States of America, vol. 111, No. 11, pp. 11467-11472, 2014.
Bullard, D.R., et al., "Direct comparison of nick-joining activity of the nucleic acid ligases from bacteriophage T4", Biochem J, vol. 398, pp. 135-144, 2006.
Burroughs, A.M., et al., "Deep-sequencing of human Argonaute-associated small RNAs provides insight into miRNA sorting and reveals Argonaute association with RNA fragments of diverse origin", RNA Biol, vol. 8, No. 1, pp. 158-177, 2011.
Chen, C., et al., "Real-time quantification of microRNAs by stem-loop RT-PCR", Nucleic Acids Res, vol. 33, No. 20, e179, 9 pages, 2005.
Clepet, C., "RNA captor: a tool for RNA characterization", PloS One, vol. 6, No. 4, e18445, 7 pages, 2011.
Cloonan, N., et al., "MicroRNAs and their isomiRs function cooperatively to target common biological pathways", Genome Biology, vol. 12, R126, 20 pages, 2011.
Czech, B., et al., "Hierarchical rules for Argonaute loading in *Drosophila*", Molecular Cell, vol. 36, No. 3, pp. 445-456, 2009.
Esteller, M., "Non-coding RNAs in human disease", Nat Rev Genet, vol. 12, pp. 861-874, 2011.
Farazi, T.A., et al., "The growing catalog of small RNAs and their association with distinct Argonaute/Piwi family members", Development, vol. 135, No. 7, pp. 1201-1214, 2008.

Fernandez-Valverde, S.L., et al., "Dynamic isomiR regulation in *Drosophila* development", RNA, vol. 16, No. 10, pp. 1881-1888, 2010.
Friedman, R.C., et al., "Most mammalian mRNAs are conserved targets of microRNAs", Genome Research, vol. 19, pp. 92-105, 2009.
Ghildiyal, M., et al., "Small silencing RNAs: an expanding universe", Nat Rev Genet, vol. 10, No. 2, pp. 94-108, 2009.
Han, B.W., et al., "The 3-to-5 exoribonuclease Knabber shapes the 32 ends of microRNAs bound to *Drosophila* Argonaute1", Current Biology, vol. 21, No. 22, pp. 1878-1887, 2011.
Ho, C.K., et al., "Bacteriophage T4 RNA ligase 2 (gp24.1) exemplifies a family of RNA ligases found in all phylogenetic domains", Proceedings of the National Academy of Sciences of the United States of America, vol. 99, No. 20, pp. 12709-12714, 2002.
Honda, S., et al., "Mitochondrial protein BmPAPI modulates the length of mature piRNAs", RNA, vol. 19, No. 10, pp. 1405-1418, 2013.
Honda, S., et al., "Dumbbell-PCR: a method to quantify specific small RNA variants with a single nucleotide resolution at terminal sequences", Nucleic Acids Research, vol. 43, No. 12, e77, 12 pages, 2015.
Honda, S., et al., "Four-leaf clover qRT-PCR: A convenient method for selective quantification of mature tRNA", RNA Biology, vol. 12, No. 5, pp. 501-508, 2015.
International Search Report issued in International Application No. PCT/US2016/048075 and dated Nov. 29, 2016.
Katoh, T., et al., "Selective stabilization of mammalian microRNAs by 3' adenylation mediated by the cytoplasmic poly(A) polymerase GLD-2", Genes & Development, vol. 23, pp. 433-438, 2009.
Kawaoka, S., et al., "The Bombyx ovary-derived cell line endogenously expresses PIWI/PIWI-interacting RNA complexes", RNA, vol. 15, pp. 1258-1264, 2009.
Kawahara, Y., et al., "Redirection of silencing targets by adenosine-to-inosine editing of miRNAs", Science, vol. 315, No. 5815, pp. 1137-1140, 2007.
Kozomara, A., et al., "miRBase: annotating high confidence microRNAs using deep sequencing data", Nucleic Acids Research, vol. 42, pp. D68-D73, 2014.
Kozubek, J., et al., "In-depth characterization of microRNA transcriptome in melanoma", PloS One, vol. 8, No. 9, e72699, 14 pages, 2013.
Lagos-Quintana, M., et al., "New microRNAs from mouse and human", RNA, vol. 9, pp. 175-179, 2003.
Landgraf, P., et al., "A mammalian microRNA expression atlas based on small RNA library sequencing", Cell, vol. 129, No. 7, pp. 1401-1414, 2007.
Li, T., et al., "MicroRNA-21 directly targets MARCKS and promotes apoptosis resistance and invasion in prostate cancer cells", Biochemical and Biophysical Research Communications, vol. 383, No. 3, pp. 280-285, 2009.
Liu, X., et al., "MicroRNAs: biogenesis and molecular functions", Brain Pathology, vol. 18, pp. 113-121, 2008.
Liu, N., et al., "The exoribonuclease Nibbler controls 3' end processing of microRNAs in *Drosophila*", Current Biology, vol. 21, pp. 1888-1893, 2011.
Loher, P., et al., "IsomiR Expression Profiles in Human Lymphoblastoid Cell Lines Exhibit Population and Gender Dependencies", Oncotarget, vol. 5, No. 18, pp. 8790-8802, 2014.
Lu, S., et al., "Adenylation of plant miRNAs", Nucleic Acids Research, vol. 37, No. 6, pp. 1878-1885, 2009.
Meijer, H.A., et al., "Regulation of miRNA strand selection: follow the leader?", Biochemical Society Transactions, vol. 42, No. 4, pp. 1135-1140, 2014.
Mi, S., et al., "Sorting of small RNAs into *Arabidopsis* argonaute complexes is directed by the 5' terminal nucleotide", Cell, vol. 133, pp. 116-127, 2008.
Montgomery, T.A., et al., "Specificity of ARGONAUTE7-miR390 interaction and dual functionality in TAS3 transacting siRNA formation", Cell, vol. 133, pp. 128-141, 2008.
Morin, R.D., et al., "Application of massively parallel sequencing to microRNA profiling and discovery in human embryonic stem cells", Genome Research, vol. 18, pp. 610-621, 2008.

(56) References Cited

OTHER PUBLICATIONS

Nandakumar, J., et al., "RNA substrate specificity and structure-guided mutational analysis of bacteriophage T4 RNA ligase 2", J Biol Chem, vol. 279, No. 30, pp. 31337-31347, 2004.

Nandakumar, et al., "Dual mechanisms whereby a broken RNA end assists the catalysis of its repair by T4 RNA ligase 2", J Biol Chem, vol. 280, No. 25, pp. 23484-23489, 2005.

Neilsen, C.T., et al., "IsomiRs—the overlooked repertoire in the dynamic microRNAome", Trends in Genetics, vol. 28, No. 11, pp. 544-549, 2012.

Newman, M.A., et al., "Deep sequencing of microRNA precursors reveals extensive 3' end modification", RNA, vol. 17, pp. 1795-1803, 2011.

Okamura, K., et al., "Endogenous small interfering RNAs in animals", Nat Rev Mol Cell Biol, vol. 9, No. 9, pp. 673-678, 2008.

Park, K., et al., "Detection of single-base mutation in RNA using T4 RNA ligase-based nick-joining or DNAzyme-based nick-generation", Analytical Biochemistry, vol. 414, No. 2, pp. 303-305, 2011.

Pillai, R.S., et al., "Repression of protein synthesis by miRNAs: how many mechanisms?", Trends Cell Biol, vol. 17, No. 3, pp. 118-126, 2007.

Ranade, K., et al., "High-throughput genotyping with single nucleotide polymorphisms", Genome Research, vol. 11, pp. 1262-1268, 2001.

Riaz, M., et al., "miRNA expression profiling of 51 human breast cancer cell lines reveals subtype and driver mutation-specific miRNAs", Breast Cancer Research, vol. 15, R33, 17 pages, 2013.

Schamberger, A., et al., "3' IsomiR species and DNA contamination influence reliable quantification of microRNAs by stem-loop quantitative PCR", PLoS One, vol. 9, No. 8, e106315, 13 pages, 2014.

Shigematsu, M., et al., "Transfer RNA as a Source of Small Functional RNA", Journal of Molecular Biology and Molecular Imaging, vol. 1, No. 2, 15 pages, 2014.

Siomi, M.C., et al., "PIWI-interacting small RNAs: the vanguard of genome defence", Nat Rev Mol Cell Biol, vol. 12, pp. 246-258, 2011.

* cited by examiner ial and physi-

SEQUENCE LISTING

<160> NUMBER OF SEQ ID NOS: 69

<210> SEQ ID NO 1
<211> LENGTH: 38
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (33)..(38)
<223> OTHER INFORMATION: n is a, c, g, or t

<400> SEQUENCE: 1
ctcagtgcag ggtccgaggt attcgcactg agnnnnnn                38

<210> SEQ ID NO 2
<211> LENGTH: 51
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: misc_feature
<222> LOCATION: (50)..(51)
<223> OTHER INFORMATION: A and G of position 50 & 51 respectively belongs to RNA

<400> SEQUENCE: 2
nnnnnnctca gtgcatggga gggtgtgtgg tcttgcttgg tgtgcactga g                51

<210> SEQ ID NO 3
<211> LENGTH: 40
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (1)..(16)
<223> OTHER INFORMATION: n is a, c, g, t or u
<220> FEATURE:
<221> NAME/KEY: misc_feature
<222> LOCATION: (39)..(40)

```
<223> OTHER INFORMATION: C and G of position 39 & 40 respectively
      belongs to RNA

<400> SEQUENCE: 3
nnnnnnnnnn nnnnnncgtc gtggagtgtg tgctttgacg                          40

<210> SEQ ID NO 4
<211> LENGTH: 50
<212> TYPE: DNA
<213> ORGANISM: Artificial Sequence
<220> FEATURE:
<223> OTHER INFORMATION: Homo sapiens

<400> SEQUENCE: 4
gtcgtatcca gtgcagggtc cgaggtattc gcactggata cgaccgccaa              50

<210> SEQ ID NO 5
<211> LENGTH: 22
<212> TYPE: RNA
<213> ORGANISM: Artificial Sequence
<220> FEATURE:
<223> OTHER INFORMATION: Homo sapiens

<400> SEQUENCE: 5
uagcagcacg uaaauauugg cg                                            22

<210> SEQ ID NO 6
<211> LENGTH: 23
<212> TYPE: RNA
<213> ORGANISM: Artificial Sequence
<220> FEATURE:
<223> OTHER INFORMATION: Homo sapiens

<400> SEQUENCE: 6
uuagcagcac guaaauauug gcg                                           23

<210> SEQ ID NO 7
<211> LENGTH: 23
<212> TYPE: RNA
<213> ORGANISM: Artificial Sequence
<220> FEATURE:
<223> OTHER INFORMATION: Homo sapiens

<400> SEQUENCE: 7
uagcagcacg uaaauauugg cgg                                           23

<210> SEQ ID NO 8
<211> LENGTH: 21
<212> TYPE: RNA
<213> ORGANISM: Artificial Sequence
<220> FEATURE:
<223> OTHER INFORMATION: Homo sapiens

<400> SEQUENCE: 8
uagcagcacg uaaauauugg c                                             21

<210> SEQ ID NO 9
<211> LENGTH: 22
<212> TYPE: RNA
<213> ORGANISM: Artificial Sequence
<220> FEATURE:
<223> OTHER INFORMATION: Homo sapiens

<400> SEQUENCE: 9
uuagcagcac guaaauauug gc                                            22
```

```
<210> SEQ ID NO 10
<211> LENGTH: 22
<212> TYPE: RNA
<213> ORGANISM: Artificial Sequence
<220> FEATURE:
<223> OTHER INFORMATION: Homo sapiens

<400> SEQUENCE: 10
agcagcacgu aaauauuggc gg                                              22

<210> SEQ ID NO 11
<211> LENGTH: 21
<212> TYPE: DNA
<213> ORGANISM: Artificial Sequence
<220> FEATURE:
<223> OTHER INFORMATION: Homo sapiens

<400> SEQUENCE: 11
gccaatattt acgtgctgct a                                               21

<210> SEQ ID NO 12
<211> LENGTH: 24
<212> TYPE: DNA
<213> ORGANISM: Artificial Sequence
<220> FEATURE:
<223> OTHER INFORMATION: Homo sapiens

<400> SEQUENCE: 12
ctcagtgcga atacctcgga ccct                                            24

<210> SEQ ID NO 13
<211> LENGTH: 15
<212> TYPE: DNA
<213> ORGANISM: Artificial Sequence
<220> FEATURE:
<223> OTHER INFORMATION: Homo sapiens

<400> SEQUENCE: 13 cgaataccte ggacc                                                      15

<210> SEQ ID NO 14
<211> LENGTH: 16
<212> TYPE: DNA
<213> ORGANISM: Artificial Sequence
<220> FEATURE:
<223> OTHER INFORMATION: Homo sapiens

<400> SEQUENCE: 14
gagggtgtgt ggtctt                                                     16

<210> SEQ ID NO 15
<211> LENGTH: 23
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (20)..(23)
<223> OTHER INFORMATION: n is a, g, c, t or u

<400> SEQUENCE: 15
tggagtgtgt gctttgacgn nnn                                             23

<210> SEQ ID NO 16
<211> LENGTH: 21
```

```
<212> TYPE: DNA
<213> ORGANISM: Artificial Sequence
<220> FEATURE:
<223> OTHER INFORMATION: Homo sapiens

<400> SEQUENCE: 16
tcgcttcggc agcacatata c                                              21

<210> SEQ ID NO 17
<211> LENGTH: 21
<212> TYPE: DNA
<213> ORGANISM: Artificial Sequence
<220> FEATURE:
<223> OTHER INFORMATION: Homo sapiens

<400> SEQUENCE: 17
cgaatttgcg tgtcatcctt g                                              21

<210> SEQ ID NO 18
<211> LENGTH: 38
<212> TYPE: DNA
<213> ORGANISM: Artificial Sequence
<220> FEATURE:
<223> OTHER INFORMATION: Homo sapiens

<400> SEQUENCE: 18
ctcagtgcag ggtccgaggt attcgcactg agcgccaa                            38

<210> SEQ ID NO 19
<211> LENGTH: 24
<212> TYPE: DNA
<213> ORGANISM: Artificial Sequence
<220> FEATURE:
<223> OTHER INFORMATION: Homo sapiens

<400> SEQUENCE: 19
ctcagtgcga atacctcgga ccct                                           24

<210> SEQ ID NO 20
<211> LENGTH: 21
<212> TYPE: DNA
<213> ORGANISM: Artificial Sequence
<220> FEATURE:
<223> OTHER INFORMATION: Homo sapiens

<400> SEQUENCE: 20
gcgctagcag cacgtaaata t                                              21

<210> SEQ ID NO 21
<211> LENGTH: 12
<212> TYPE: DNA
<213> ORGANISM: Artificial Sequence
<220> FEATURE:
<223> OTHER INFORMATION: Homo sapiens

<400> SEQUENCE: 21
tggcgctcag tg                                                        12

<210> SEQ ID NO 22
<211> LENGTH: 38
<212> TYPE: DNA
<213> ORGANISM: Artificial Sequence
<220> FEATURE:
<223> OTHER INFORMATION: Homo sapiens

<400> SEQUENCE: 22
```
ctcagtgcag ggtccgaggt attcgcactg aggttcga                              38

<210> SEQ ID NO 23
<211> LENGTH: 18
<212> TYPE: DNA
<213> ORGANISM: Artificial Sequence
<220> FEATURE:
<223> OTHER INFORMATION: Homo sapiens

<400> SEQUENCE: 23
tcaaaaacta acggattg                                                    18

<210> SEQ ID NO 24
<211> LENGTH: 16
<212> TYPE: DNA
<213> ORGANISM: Artificial Sequence
<220> FEATURE:
<223> OTHER INFORMATION: Homo sapiens

<400> SEQUENCE: 24
tcgaacctca gtgcag                                                      16

<210> SEQ ID NO 25
<211> LENGTH: 38
<212> TYPE: DNA
<213> ORGANISM: Artificial Sequence
<220> FEATURE:
<223> OTHER INFORMATION: Homo sapiens

<400> SEQUENCE: 25
ctcagtgcag ggtccgaggt attcgcactg aggactgt                              38

<210> SEQ ID NO 26
<211> LENGTH: 17
<212> TYPE: DNA
<213> ORGANISM: Artificial Sequence
<220> FEATURE:
<223> OTHER INFORMATION: Homo sapiens

<400> SEQUENCE: 26
aacagtcctc agtgcag                                                     17

<210> SEQ ID NO 27
<211> LENGTH: 38
<212> TYPE: DNA
<213> ORGANISM: Artificial Sequence
<220> FEATURE:
<223> OTHER INFORMATION: Homo sapiens

<400> SEQUENCE: 27
ctcagtgcag ggtccgaggt attcgcactg agccgcag                              38

<210> SEQ ID NO 28
<211> LENGTH: 18
<212> TYPE: DNA
<213> ORGANISM: Artificial Sequence
<220> FEATURE:
<223> OTHER INFORMATION: Homo sapiens

<400> SEQUENCE: 28
aaaagcatga gaatttgc                                                    18

<210> SEQ ID NO 29
<211> LENGTH: 15
<212> TYPE: DNA
<213> ORGANISM: Artificial Sequence

```
<220> FEATURE:
<223> OTHER INFORMATION: Homo sapiens

<400> SEQUENCE: 29
ctgcggctca gtgca                                                    15

<210> SEQ ID NO 30
<211> LENGTH: 38
<212> TYPE: DNA
<213> ORGANISM: Artificial Sequence
<220> FEATURE:
<223> OTHER INFORMATION: Homo sapiens

<400> SEQUENCE: 30
ctcagtgcag ggtccgaggt attcgcactg agtggtcc                           38

<210> SEQ ID NO 31
<211> LENGTH: 17
<212> TYPE: DNA
<213> ORGANISM: Artificial Sequence
<220> FEATURE:
<223> OTHER INFORMATION: Homo sapiens

<400> SEQUENCE: 31
cggaccactc agtgcag                                                  17

<210> SEQ ID NO 32
<211> LENGTH: 51
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (50)..(51)
<223> OTHER INFORMATION: A and G of position 50 & 51 respectively
      belongs to RNA

<400> SEQUENCE: 32
ctgctactca gtgcgtggga gggtgtgtgg tcttgcttgg tgtgcactga g            51

<210> SEQ ID NO 33
<211> LENGTH: 20
<212> TYPE: DNA
<213> ORGANISM: Artificial Sequence
<220> FEATURE:
<223> OTHER INFORMATION: Homo sapiens

<400> SEQUENCE: 33
gcgacgccaa tatttacgtg                                               20

<210> SEQ ID NO 34
<211> LENGTH: 17
<212> TYPE: DNA
<213> ORGANISM: Artificial Sequence
<220> FEATURE:
<223> OTHER INFORMATION: Homo sapiens

<400> SEQUENCE: 34
tgtgcactga gtagcag                                                  17

<210> SEQ ID NO 35
<211> LENGTH: 51
<212> TYPE: DNA
<213> ORGANISM: Artificial Sequence
<220> FEATURE:
<223> OTHER INFORMATION: Homo sapiens
```

```
<220> FEATURE:
<221> NAME/KEY: misc_feature
<222> LOCATION: (50)..(51)
<223> OTHER INFORMATION: A and G of position 50 & 51 respectively
      belongs to RNA

<400> SEQUENCE: 35
cttgaactca gtgcgtggga gggtgtgtgg tcttgcttgg tgtgcactga g         51

<210> SEQ ID NO 36
<211> LENGTH: 17
<212> TYPE: DNA
<213> ORGANISM: Artificial Sequence
<220> FEATURE:
<223> OTHER INFORMATION: Homo sapiens

<400> SEQUENCE: 36
cagcctatcc tggatta                                               17

<210> SEQ ID NO 37
<211> LENGTH: 17
<212> TYPE: DNA
<213> ORGANISM: Artificial Sequence
<220> FEATURE:
<223> OTHER INFORMATION: Homo sapiens

<400> SEQUENCE: 37
tgtgcactga gttcaag                                               17

<210> SEQ ID NO 38
<211> LENGTH: 51
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (50)..(51)
<223> OTHER INFORMATION: A and G of position 50 & 51 respectively
      belongs to RNA

<400> SEQUENCE: 38
ttgaatctca gtgcgtggga gggtgtgtgg tcttgcttgg tgtgcactga g         51

<210> SEQ ID NO 39
<211> LENGTH: 30
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (29)..(30)
<223> OTHER INFORMATION: C and G of position 30 & 31 respectively
      belongs to RNA
<220> FEATURE:
<221> NAME/KEY: misc_feature
<222> LOCATION: (29)..(30)
<223> OTHER INFORMATION: C and G of position 29 & 30 respectively
      belongs to RNA

<400> SEQUENCE: 39
ctgctacgtc gtggagtgtg tgctttgacg                                 30

<210> SEQ ID NO 40
<211> LENGTH: 36
<212> TYPE: DNA
<213> ORGANISM: Artificial Sequence
<220> FEATURE:
```

<223> OTHER INFORMATION: Homo sapiens
<220> FEATURE:
<221> NAME/KEY: misc_feature
<222> LOCATION: (35)..(36)
<223> OTHER INFORMATION: C and G of position 35 & 36 respectively
      belongs to RNA

<400> SEQUENCE: 40
tacgtgctgc tacgtcgtgg agtgtgtgct ttgacg                      36

<210> SEQ ID NO 41
<211> LENGTH: 40
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (39)..(40)
<223> OTHER INFORMATION: C and G of position 39 & 40 respectively
      belongs to RNA

<400> SEQUENCE: 41
tatttacgtg ctgctacgtc gtggagtgtg tgctttgacg                  40

<210> SEQ ID NO 42
<211> LENGTH: 38
<212> TYPE: DNA
<213> ORGANISM: Artificial Sequence
<220> FEATURE:
<223> OTHER INFORMATION: Homo sapiens

<400> SEQUENCE: 42
ctcagtgcag ggtccgaggt attcgcactg agcgccaa                    38

<210> SEQ ID NO 43
<211> LENGTH: 23
<212> TYPE: DNA
<213> ORGANISM: Artificial Sequence
<220> FEATURE:
<223> OTHER INFORMATION: Homo sapiens

<400> SEQUENCE: 43
tggagtgtgt gctttgacgt agc                                    23

<210> SEQ ID NO 44
<211> LENGTH: 20
<212> TYPE: DNA
<213> ORGANISM: Artificial Sequence
<220> FEATURE:
<223> OTHER INFORMATION: Homo sapiens

<400> SEQUENCE: 44
aaatattggc gctcagtgca                                        20

<210> SEQ ID NO 45
<211> LENGTH: 40
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (39)..(40)
<223> OTHER INFORMATION: C and G of position 39 & 40 respectively
      belongs to RNA

<400> SEQUENCE: 45

-continued tcagtctgat aagctacgtc gtggagtgtg tgctttgacg         40

<210> SEQ ID NO 46
<211> LENGTH: 38
<212> TYPE: DNA
<213> ORGANISM: Artificial Sequence
<220> FEATURE:
<223> OTHER INFORMATION: Homo sapiens

<400> SEQUENCE: 46
ctcagtgcag ggtccgaggt attcgcactg agtcaaca         38

<210> SEQ ID NO 47
<211> LENGTH: 21
<212> TYPE: DNA
<213> ORGANISM: Artificial Sequence
<220> FEATURE:
<223> OTHER INFORMATION: Homo sapiens

<400> SEQUENCE: 47
agactgatgt tgctcagtgc a         21

<210> SEQ ID NO 48
<211> LENGTH: 40
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (39)..(40)
<223> OTHER INFORMATION: C and G of position 39 & 40 respectively
      belongs to RNA

<400> SEQUENCE: 48
aaattctcat gcttttcgtc gtggagtgtg tgctttgacg         40

<210> SEQ ID NO 49
<211> LENGTH: 38
<212> TYPE: DNA
<213> ORGANISM: Artificial Sequence
<220> FEATURE:
<223> OTHER INFORMATION: Homo sapiens

<400> SEQUENCE: 49
ctcagtgcag ggtccgaggt attcgcactg agccgcag         38

<210> SEQ ID NO 50
<211> LENGTH: 24
<212> TYPE: DNA
<213> ORGANISM: Artificial Sequence
<220> FEATURE:
<223> OTHER INFORMATION: Homo sapiens

<400> SEQUENCE: 50
tggagtgtgt gctttgacga aaag         24

<210> SEQ ID NO 51
<211> LENGTH: 15
<212> TYPE: DNA
<213> ORGANISM: Artificial Sequence
<220> FEATURE:
<223> OTHER INFORMATION: Homo sapiens

<400> SEQUENCE: 51
ctgcggctca gtgca         15

<210> SEQ ID NO 52
<211> LENGTH: 40
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (39)..(40)
<223> OTHER INFORMATION: C and G of position 39 & 40 respectively
      belongs to RNA

<400> SEQUENCE: 52
aaattctcat gcttttcgtc gtggagtgtg tgctttgacg                40

<210> SEQ ID NO 53
<211> LENGTH: 38
<212> TYPE: DNA
<213> ORGANISM: Artificial Sequence
<220> FEATURE:
<223> OTHER INFORMATION: Homo sapiens

<400> SEQUENCE: 53
ctcagtgcag ggtccgaggt attcgcactg agtggtcc                 38

<210> SEQ ID NO 54
<211> LENGTH: 26
<212> TYPE: RNA
<213> ORGANISM: Artificial Sequence
<220> FEATURE:
<223> OTHER INFORMATION: Homo sapiens

<400> SEQUENCE: 54
ucaaaacuaa cggauugguu ucgaac                              26

<210> SEQ ID NO 55
<211> LENGTH: 30
<212> TYPE: RNA
<213> ORGANISM: Artificial Sequence
<220> FEATURE:
<223> OTHER INFORMATION: Homo sapiens

<400> SEQUENCE: 55
ucaaaacuaa cggauugguu ucgaacaguc                          30

<210> SEQ ID NO 56
<211> LENGTH: 27
<212> TYPE: RNA
<213> ORGANISM: Artificial Sequence
<220> FEATURE:
<223> OTHER INFORMATION: Homo sapiens

<400> SEQUENCE: 56
aaaagcauga gaauuugcug ucugcgg                             27

<210> SEQ ID NO 57
<211> LENGTH: 31
<212> TYPE: RNA
<213> ORGANISM: Artificial Sequence
<220> FEATURE:
<223> OTHER INFORMATION: Homo sapiens

<400> SEQUENCE: 57
aaaagcauga gaauuugcug ucugcggacc a                        31

<210> SEQ ID NO 58

<211> LENGTH: 21
<212> TYPE: RNA
<213> ORGANISM: Artificial Sequence
<220> FEATURE:
<223> OTHER INFORMATION: Homo sapiens

<400> SEQUENCE: 58
agcagcacgu aaauauuggc g                                          21

<210> SEQ ID NO 59
<211> LENGTH: 22
<212> TYPE: RNA
<213> ORGANISM: Artificial Sequence
<220> FEATURE:
<223> OTHER INFORMATION: Homo sapiens

<400> SEQUENCE: 59
uucaaguaau ccaggauagg cu                                         22

<210> SEQ ID NO 60
<211> LENGTH: 23
<212> TYPE: RNA
<213> ORGANISM: Artificial Sequence
<220> FEATURE:
<223> OTHER INFORMATION: Homo sapiens

<400> SEQUENCE: 60
auucaaguaa uccaggauag gcu                                        23

<210> SEQ ID NO 61
<211> LENGTH: 21
<212> TYPE: RNA
<213> ORGANISM: Artificial Sequence
<220> FEATURE:
<223> OTHER INFORMATION: Homo sapiens

<400> SEQUENCE: 61
agcagcacgu aaauauuggc g                                          21

<210> SEQ ID NO 62
<211> LENGTH: 17
<212> TYPE: DNA
<213> ORGANISM: Artificial Sequence
<220> FEATURE:
<223> OTHER INFORMATION: Homo sapiens

<400> SEQUENCE: 62
tgtgcactga gattcaa                                               17

<210> SEQ ID NO 63
<211> LENGTH: 38
<212> TYPE: DNA
<213> ORGANISM: Artificial Sequence
<220> FEATURE:
<223> OTHER INFORMATION: Homo sapiens

<400> SEQUENCE: 63
ctcagtgcag ggtccgaggt attcgcactg aggttcca                        38

<210> SEQ ID NO 64
<211> LENGTH: 27
<212> TYPE: RNA
<213> ORGANISM: Artificial Sequence
<220> FEATURE:
<223> OTHER INFORMATION: Homo sapiens

<400> SEQUENCE: 64

```
ucaaaaacua acggauuggu uucgaac                                    27

<210> SEQ ID NO 65
<211> LENGTH: 31
<212> TYPE: RNA
<213> ORGANISM: Artificial Sequence
<220> FEATURE:
<223> OTHER INFORMATION: Homo sapiens

<400> SEQUENCE: 65
ucaaaaacua acggauuggu uucgaacagu c                               31

<210> SEQ ID NO 66
<211> LENGTH: 51
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (50)..(51)
<223> OTHER INFORMATION: A and G of position 50 & 51 respectively
      belongs to RNA

<400> SEQUENCE: 66
cttgaactca gtgcatggga gggtgtgtgg tcttgcttgg tgtgcactga g         51

<210> SEQ ID NO 67
<211> LENGTH: 22
<212> TYPE: RNA
<213> ORGANISM: Artificial Sequence
<220> FEATURE:
<223> OTHER INFORMATION: Homo sapiens

<400> SEQUENCE: 67
uagcuuauca gacugauguu ga                                         22

<210> SEQ ID NO 68
<211> LENGTH: 36
<212> TYPE: DNA
<213> ORGANISM: Artificial Sequence
<220> FEATURE:
<223> OTHER INFORMATION: Homo sapiens

<400> SEQUENCE: 68
ctcagtgcag ggtccgaggt attcgcactg agtcaa                          36

<210> SEQ ID NO 69
<211> LENGTH: 42
<212> TYPE: DNA
<213> ORGANISM: Artificial Sequence
<220> FEATURE:
<223> OTHER INFORMATION: Homo sapiens
<220> FEATURE:
<221> NAME/KEY: misc_feature
<222> LOCATION: (40)..(41)
<223> OTHER INFORMATION: A and C of position 40 & 41 respectively
      belongs to RNA

<400> SEQUENCE: 69
catcagtctg ataagctacg tcgtggagtg tgtgctttga cg                   42
```

DUMBBELL-PCR: A METHOD TO QUANTIFY SPECIFIC SMALL RNA VARIANTS WITH A SINGLE NUCLEOTIDE RESOLUTION AT TERMINAL SEQUENCES

CROSS REFERENCE TO RELATED APPLICATIONS

This application is a National Phase under 35 U.S.C. 371 of International Application No. PCT/US16/48075, filed Aug. 22, 2016, which claims the benefit of provisional application No. 62/208,183, filed Aug. 21, 2015, the contents of which are herein incorporated by reference.

REFERENCE TO AN ELECTRONIC SEQUENCE LISTING

The contents of the electronic sequence listing (U.S. Ser. No. 15/754,194.txt; Size: 14,630 bytes; and Date of Creation: Jun. 11, 2021) is herein incorporated by reference in its entirety.

SEQUENCE LISTING

The instant application contains a Sequence Listing which has been submitted in ST.25 Text File Format via EFS-WEB and is hereby incorporated by reference in its entirety.

FIELD OF INVENTION

The present application is generally related to methods for quantifying RNA variants with specific terminal sequences.

BACKGROUND OF THE INVENTION

Non-protein-coding regions of the genome are widely transcribed to produce non-coding RNAs (ncRNAs), which play crucial roles in normal biological processes and disease states (1). Within the diverse group of ncRNAs, the functional significance is particularly evident for small regulatory RNAs which direct highly specific regulation of gene expression by recognizing complementary RNA targets. Thus far, three major classes of small regulatory RNAs have been particularly studied in depth: microRNAs (miRNAs), short-interfering RNAs (siRNAs), and PIWI-interacting RNAs (piRNAs) (2-6). The defining features of these RNA classes are the short lengths of 20-31 nucleotides (nt), and interactions with Argonaute family proteins, which can be divided into AGO and PIWI subclasses, to form effector ribonucleoprotein complexes. miRNAs, the best-studied class of small regulatory RNAs, are produced from stem-loop hairpin-structured precursor RNAs, which are processed by the ribonucleases Drosha and Dicer. The ~22-nt mature miRNAs interact with AGO proteins and recognize complementary sequences in the target mRNAs, which are often located in the 3'-UTR. This recognition results in the deposition of the AGO/miRNA effector complex on the target mRNA, principally resulting in repression of target gene expression (7, 8). For target recognition by miRNAs, full complementarity between the miRNA and its target is not required, although base pairing of nucleotides at 2-8 positions of the miRNA, the so-called seed region, is generally essential (2). The human genome encodes over 2,000 miRNAs (9), which are estimated to regulate the expression of most protein-coding genes (10), thereby exhibiting a tremendous impact on normal developmental and physiological processes and disease states.

Recent advances in next-generation sequencing (NGS) technologies have revealed the complex heterogeneity of the length and terminal sequences among the majority of mature miRNAs; identical miRNA genes encode mature isomers termed isomiRs that vary in size by one or more nucleotides at the 5'- and/or 3'-end of the miRNA (5'-isomiRs and/or 3'-isomiRs, respectively) (11-13). These isomiRs can be generated by several mechanisms during miRNA biogenesis, including variable processing by Dicer or Drosha cleavage and post-transcriptional modifications, such as nontemplated nucleotide addition, exonuclease-derived trimming, and RNA editing (14-19). It has been increasingly apparent that the isomiR expression is functionally significant. IsomiRs have been shown to associate with AGO proteins (20-23), and terminal variations of isomiRs influence the AGO protein species on which each isomiR is loaded (2427). Moreover, 5'-isomiRs have been reported to differentially recognize specific target mRNAs compared with canonical miRNAs due to shifts of the critical seed region (21). Variation of 5'-terminal sequences may also affect the selection of miRNA/miRNA strands for AGO loading due to changes in the relative thermodynamic stability of the duplex ends (28).

Moreover, variations to the 3'-ends of miRNAs to produce 3'-isomiRs are also crucial for gene expression regulation because post-transcriptional nontemplate 3'-end addition of uridines and adenosines markedly alters miRNA stability (29-31). Supporting the importance of terminal heterogeneity of miRNAs, isomiRs are differentially expressed across different cell and tissue types in different developmental stages (32-36). Notably, expression of human isomiRs in lymphoblastoid cells are subjected to population- and gender-based pressures (23).

To unravel the emerging complexities of small RNA heterogeneity and molecular mechanisms underlying them, accurate quantification of individual small RNA variants and easy analysis of their expression profiles are imperative. Microarray analysis of miRNAs is insufficient to completely distinguish miRNAs from their corresponding isomiRs. Although NGS can adequately capture the entire repertoire of miRNAs and their corresponding isomiRs, the required cost, time, and subsequent bioinformatics analyses could preclude the use of NGS for only examining specific focused isomiRs. In Northern blot analysis, distinguishing different isomiRs with the same or similar lengths is difficult. The TaqMan® RT-PCR assay using stem-loop primers (37), which is widely used to quantify miRNAs, is not able to discriminate differences in miRNA terminal sequences of only 1 nt (38). Thus, a novel method for quick and efficient quantification for small RNA variants is required.

Accordingly, in view of the recent advances in next-generation sequencing technologies, which have revealed that cellular functional RNAs are not always expressed as single entities with fixed terminal sequences, but as multiple isoforms bearing complex heterogeneity in both length and terminal sequences, such as isomiRs, the isoforms of microRNAs, there is a need for unraveling the biogenesis and biological significance of heterogenetic RNA expression, which requires distinctive analysis of each RNA variant. Therefore, Db-PCR provides a much-needed simple method for analyzing RNA terminal heterogeneity and possesses broad applicability for the quantification of various small RNAs in different cell types, consistent with results from other quantification methods.

SUMMARY OF THE INVENTION

The methods described herein related to Dumbbell-PCR (Db-PCR), a TaqMan®-qRT-PCR-based method which is able to specifically and efficiently quantify the expression of targeted RNA variants with specific terminal sequences. Because cellular functional RNAs are expressed as multiple isoforms bearing complex heterogeneity in terminal sequences and the heterogeneity plays crucial roles in the expression and function of the RNAs, distinctive analysis of each RNA variant by Db-PCR will greatly contribute to RNA expression analyses in cells and tissues.

In accordance with these and other objects, a first embodiment of an invention disclosed herein is directed to a method of quantifying RNA variants with specific terminal sequences comprising: applying 5'- and 3'-stem-loop adapters, specifically hybridized and ligated to the 5'- and 3'-ends of target RNAs, respectively, by T4 RNA ligase 2 (Rnl2) to create ligation products with "dumbbell-like" structures; subsequently these structures are quantified by TaqMan® RT-PCR; wherein the high specificity of Rnl2 ligation and TaqMan® RT-PCR toward target RNAs assured both 5'- and 3'-terminal sequences of target RNAs with single nucleotide resolution so that Db-PCR specifically detected target RNAs but not their corresponding terminal variants.

A further embodiment is directed to a method, termed Db-PCR, to quantify specific small RNA variants with a single nucleotide resolution at terminal sequences comprising: hybridizing a 5'-Dbs-adapter to the 5'-end of target RNAs, wherein the 5'-Dbs-adapter has a stem-loop structure whose protruding 5'-end base-pairs 5'-end of target RNAs, and wherein the loop region of 5'-Dbs-adapter contains a base-lacking spacer which will terminate reverse transcription in a subsequent step; hybridizing a 3'-Db-adapter to the 3'-end of target RNAs, wherein the 3'-Db-adapter has a stem-loop structure whose protruding 3'-end base-pairs 3'-end of target RNAs; ligating the both adapters with target RNAs by Rnl2 ligation to form "dumbbell-like" structure; and, amplifying and quantifying the ligation product by TaqMan® RT-PCR.

A further method, termed 5'-Db-PCR, is directed to quantifying specific small RNA variants with a single nucleotide resolution at a 5'-terminal sequence comprising: hybridizing a 5'-Db-adapter to the 5'-end of target RNAs, wherein the 5'-Db-adapter has a stem-loop structure whose protruding 5'-end base-pairs 5'-end of target RNAs; ligating the adapter with target RNAs by Rnl2 ligation; and, amplifying and quantifying the ligation product by TaqMan® RT-PCR, wherein the TaqMan® probe is designed to target the boundary of the adapter and target RNAs to exclusively quantify ligated target RNAs.

A further embodiment is directed to a method, termed 3'-Db-PCR, to quantify specific small RNA variants with a single nucleotide resolution at a 3' terminal sequence comprising: hybridizing a 3'-Db-adapter to the 3'-end of target RNAs, wherein the 3'-Db-adapter has a stem-loop structure whose protruding 3'-end base-pairs 3'-end of target RNAs; ligating the adapter with target RNAs by Rnl2 ligation; and amplifying and quantifying the ligation product by TaqMan® RT-PCR, wherein the TaqMan® probe is designed to target the boundary of the adapter and target RNAs to exclusively quantify ligated target RNAs.

A further embodiment is directed to one of the above methods wherein the TaqMan® probe is designed to target the boundary of the adapter and target RNAs to exclusively quantify ligated target RNAs.

An embodiment is directed to a method to quantify specific small RNA variants with a single nucleotide resolution at terminal sequences comprising: creating the following adapters and primers: a 5'-Dbs-adapter, whose protruding 5'-terminal 16 nucleotides are complementary to 5'-terminal sequences of a target RNA; a 3'-Db-adapter whose protruding 3'-terminal nucleotides are complementary to 3'-terminal sequences of the target RNA; a RT primer; a reverse primer; a forward primer; and a TaqMan® probe targeting the boundary of the target RNA and 3'-Db-adapter; hybridizing a 5'-Dbs-adapter to the 5'-end of the target RNA, wherein the 5'-Dbs-adapter has a stem-loop structure whose protruding 5'-end base-pairs 5'-end of target RNAs, and wherein the loop region of 5'-Dbs-adapter contains a base-lacking spacer which will terminate reverse transcription; hybridizing a 3'-Db-adapter to the 3'-end of the target RNA, wherein the 3'-Db-adapter has a stem-loop structure whose protruding 3'-end base-pairs 3'-end of the target RNA; ligating both adapters with the target RNA by Rnl2 ligation to form a "dumbbell-like" structure ligation product; and amplifying and quantifying the ligation product by TaqMan® RT-PCR.

An embodiment is directed to a method to quantify specific small RNA variants with a single nucleotide resolution at a 5'-terminal sequence comprising: creating the following adapters and primers: a 5'-Db-adapter whose protruding 5'-terminal 6 nucleotides are complementary to 5'-terminal sequences of a target RNA; a RT/R primer which is complementary to 3'-terminal sequences of the target RNA; a forward primer; and a TaqMan® probe targeting the boundary of the target RNA and 5'-Db-adapter; hybridizing a 5'-Db-adapter to the 5'-end of target RNAs, wherein the 5'-Db-adapter has a stem-loop structure whose protruding 5'-end base-pairs 5'-end of target RNAs; ligating the adapter with target RNAs by Rnl2 ligation to form a ligation product; and amplifying and quantifying the ligation product by TaqMan® RT-PCR, wherein the TaqMan® probe is designed to target the boundary of the adapter and target RNAs to exclusively quantify ligated target RNAs.

An embodiment is directed towards a method to quantify specific small RNA variants with a single nucleotide resolution at a 3'-terminal sequence comprising: creating the following: a 3'-Db-adapter whose protruding 3'-terminal 6 nucleotides are complementary to 3'-terminal sequences of a target RNA; a RT primer; a reverse primer; a forward primer which is complementary to 5'-terminal sequences of a target RNA; and a TaqMan® probe targeting the boundary of the target RNA and 3'-Db-adapter; hybridizing a 3'-Db-adapter to the 3'-end of target RNAs, wherein the 3'-Db-adapter has a stem-loop structure whose protruding 3'-end base-pairs 3'-end of target RNAs; ligating the adapter with target RNAs by Rnl2 ligation to form a ligation product; and amplifying and quantifying the ligation product by TaqMan® RT-PCR, wherein the TaqMan® probe is designed to target the boundary of the adapter and target RNAs to exclusively quantify ligated target RNAs.

DETAILED DESCRIPTION OF THE PREFERRED EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

The present disclosure provides for novel methods of quantifying RNA variants with specific terminal sequences. The method and variations as described herein are called "Dumbbell-PCR" (Db-PCR), which is an efficient and convenient TaqMan® RT-PCR-based method with single-nucleotide resolution at both the 5'- and 3'-terminal sequences to specifically quantify individual small RNA variants. The Db-PCR procedure includes a nick-ligation step catalyzed by T4 RNA ligase 2 (Rn12) which was originally identified in the bacteriophage T4 (39). Rn12 catalyzes RNA ligation at a 3'-OH/5'-P nick in a double-stranded RNA (dsRNA) or an RNA-DNA hybrid (40-42), which makes Rn12 an attractive tool in cDNA preparation (43) and single nucleotide polymorphism detection (44).

In the examples and embodiments described herein, stem-loop adapters, termed Dumbbell adapters (Db-adapters), were specifically hybridized and ligated by Rn12 to the 5'- and 3'-ends of a targeted small RNA to generate a "dumbbell-like" structure. Subsequent TaqMan® RT-PCR was able to quantify specific target RNA without cross-reactivity to its terminal variant even with a single-nucleotide difference at the terminal sequences. Further, the studies developed 5'-Dumbbell-PCR (5'-Db-PCR) and 3'-Dumbbell-PCR (3'-Db-PCR) to specifically quantify unique variations to the 5'- and 3'-ends of individual small RNAs, respectively. These methods provide a novel, efficient, and convenient technique for specific detection and differential expression analysis of small RNA variants, such as isomiRs.

Design Scheme of Dumbbell PCRs to Quantify a Specific Variant of RNAs

Figure 6A:
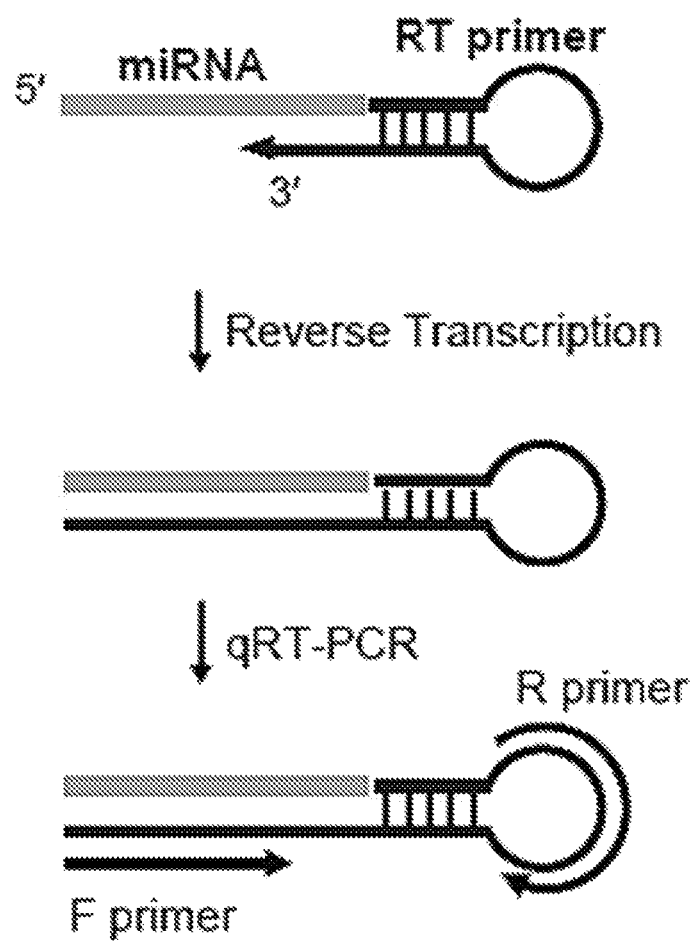
FIG. 6(A) is a schematic representation of a standard RT-PCR using a stem-loop primer for miRNA quantification.
Figure 6B:
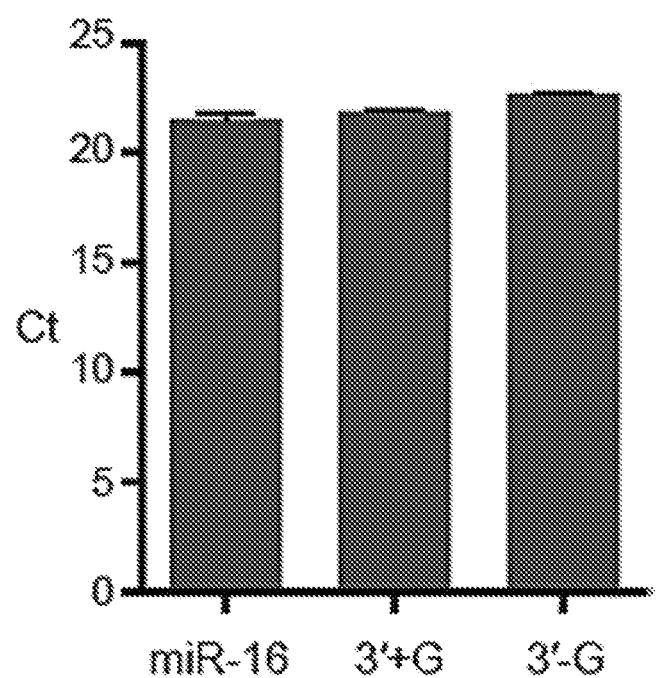
FIG. 6(B) depicts that standard RT-PCR using stem-loop primer is not capable of distinguishing 3'-variants of miRNA and (i) the miR-16 is shown in SEQ ID NO: 5, (ii) the 3'+G is shown in SEQ ID NO: 7, and (iii) the 3'−G is shown in SEQ ID NO: 8.

The TaqMan® RT-PCR using stem-loop primers is a standard method to quantify miRNAs (37). However, this method is inadequate to discriminate 5'-terminal variations of targeted miRNAs because it utilizes a forward primer derived from the interior sequences of the miRNAs (FIG. 6A). In addition, although stem-loop primer recognizes and hybridizes to the 3'-end of targeted miRNAs, experiments targeting miR-16 similarly amplified the miR-16 and its 3'-variants that either contain an additional G (miR-16-[3'+G]) or lack a G (miR-16-[3'−G]) at the 3'-end (FIG. 6B). These results, in agreement with those of previous studies (38), indicate that such methods are not capable of distinguishing 5'- and 3'-variants of small RNAs.

Figure 1A:
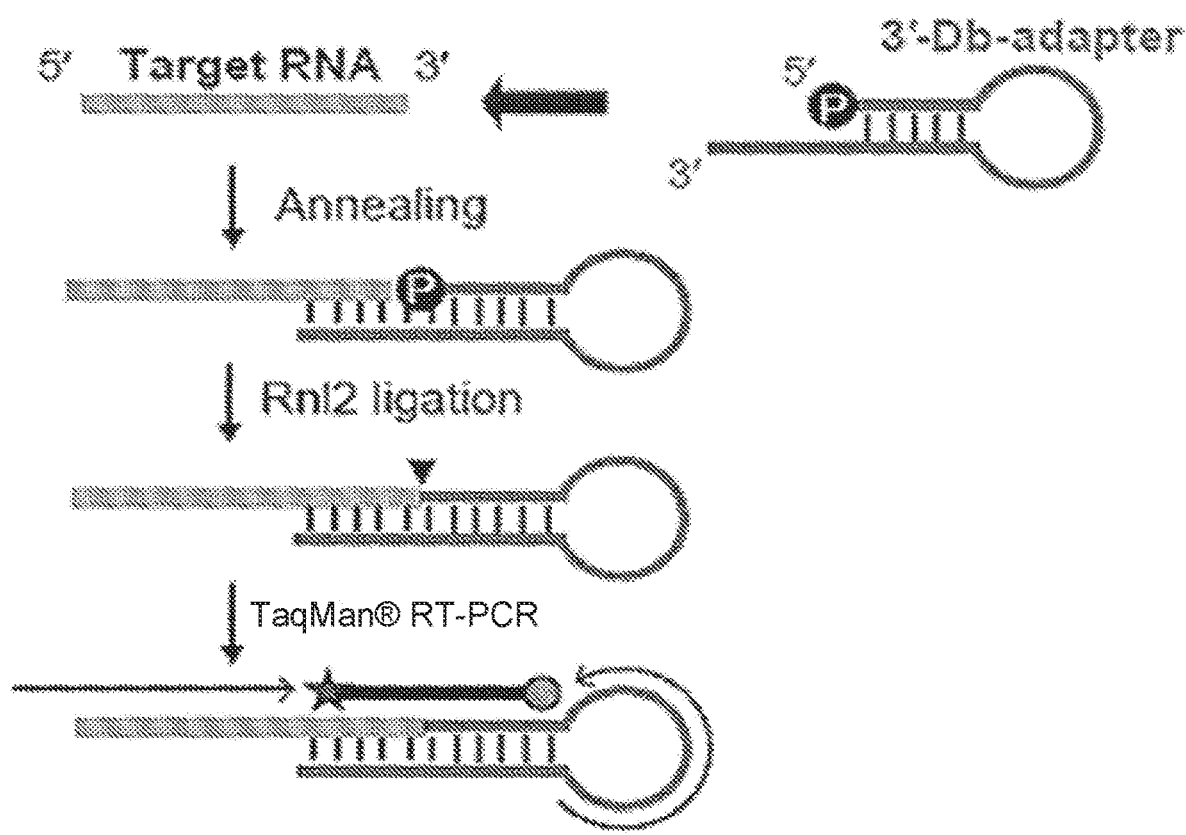
FIG. 1(A) depicts a schematic representation of 3'-Db-PCR.
Figure 1B:
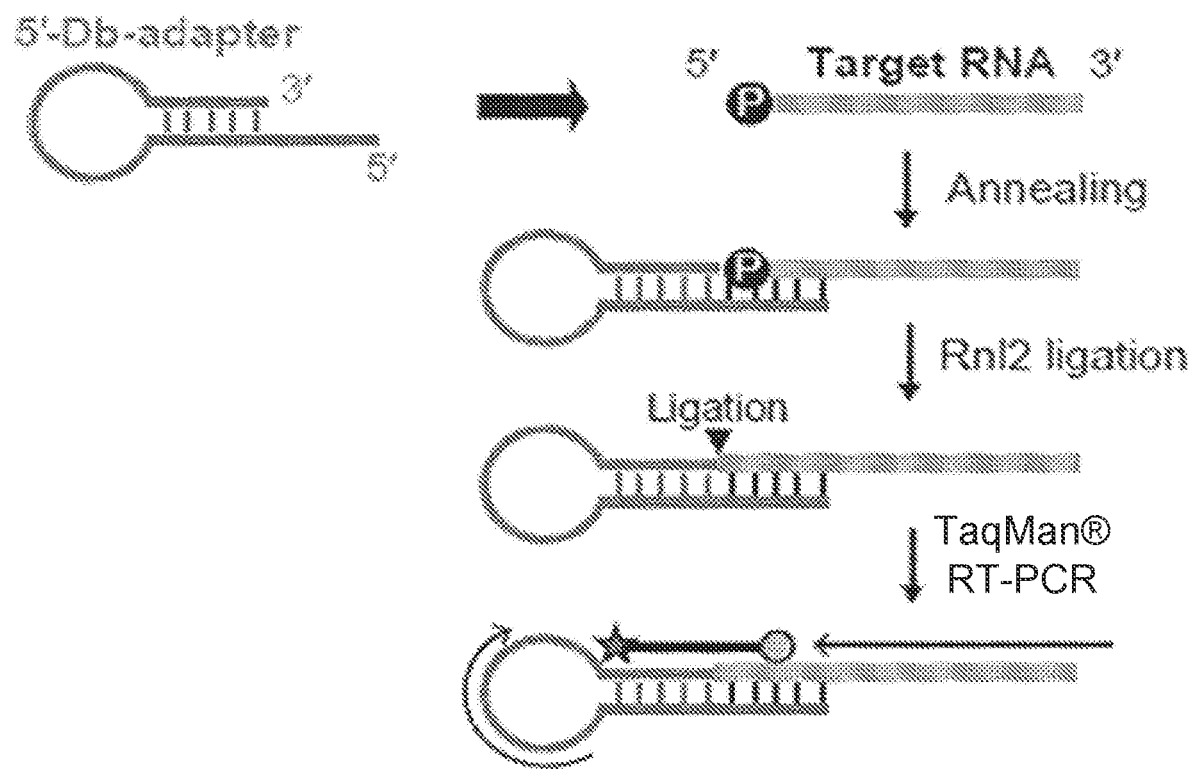
FIG. 1(B) depicts a schematic representation of 5'-Db-PCR.
Figure 2A:
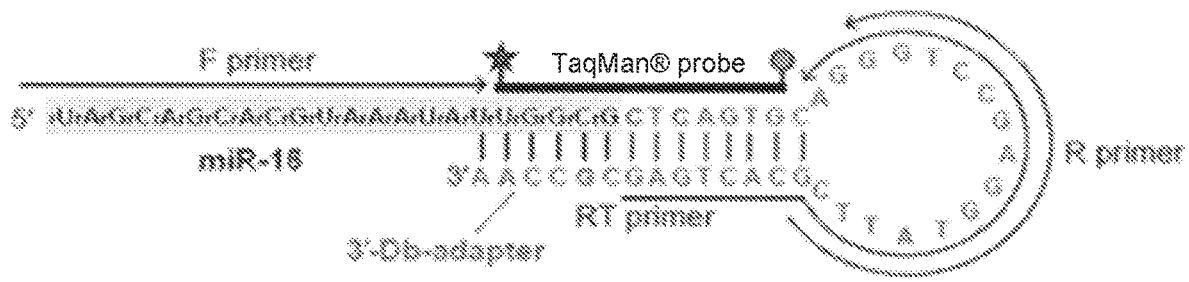
FIG. 2(A) depicts the formation of the stem-loop structure of a 3'-Db-adapter whose protruding 3'-end base-pairs with the 3'-end of target RNA and (i) the F primer is shown in SEQ ID NO: 5, (ii) the R primer is shown in SEQ ID NO: 18, (iii) the 3'-Db-adapter is shown in SEQ ID NO: 18, (iv) the RT primer is shown in SEQ ID NO: 19, (v) the TaqMan® probe is shown in SEQ ID NO: 21, and (vi) the miR-16 is shown in SEQ ID NO: 5.

Therefore, the experiments described herein designed methods of 3'-Dumbbell PCR (3'-Db-PCR, FIG. 1A) and 5'-Dumbbell PCR (5'-Db-PCR, FIG. 1B) for selective quantification of specific 3'- and 5'-variant of small RNAs, respectively. In 3'-Db-PCR, total RNA is extracted from cells and a 3'-Dumbbell adapter (3'-Db-adapter) containing protruding 3'-end is hybridized to the 3'-end of the target RNA in the total RNA. The 3'-Db-adapter consists of DNA forming a stem-loop structure with 6 nucleotides protruding from the 3'-end (FIG. 2A). Its sequences are "5'-/Phos/CTCAGTGCAGGGTCCGAGGTATTCGCACTGAGX-XXXXX-3' (SEQ ID NO: 1)". The 3'-terminal six nucleotides XXXXXX designate the sequences complementary to 3'-terminal sequences of a target RNA. The loop sequences of the 3'-Db-adapter were identical with those of a stem-loop primer for miRNA quantification (37).

Figure 3A:
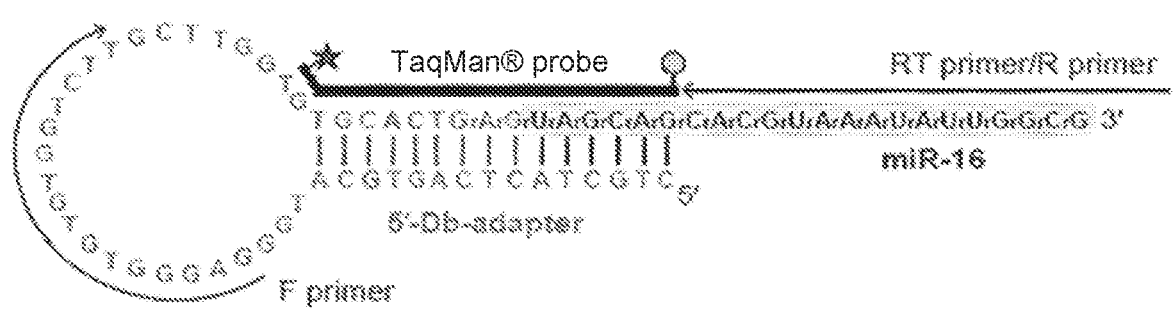
FIG. 3(A) depicts the formation of the stem-loop structure of a 5'-Db-adapter whose protruding 5'-end base-pairs with the 5'-end of target RNA and (i) the F primer is shown in SEQ ID NO: 14, (ii) the R primer is shown in SEQ ID NO: 33, (iii) the 5'-Db-adapter is shown in SEQ ID NO: 32, (iv) the RT primer is shown in SEQ ID NO: 33, (v) the TaqMan® probe is shown in SEQ ID NO: 34, and (vi) the miR-16 is shown in SEQ ID NO: 5.

In 5'-Db-PCR, a 5'-Dumbbell adapter (5'-Db-adapter) containing protruding 5'-end is hybridized to the 5'-end of the target RNA. The 5'-Db-adapter contains both DNA and RNA and forms a stem-loop structure with 6 nucleotides protruding from the 5'-end (FIG. 3A). Its sequences are "5'-XXXXXXCTCAGTGCATGGGAGGGTGTGTGGTT-TGCTTGGTGTGCACTGrArG-3' (SEQ ID NO: 2)". The 5'-terminal six nucleotides XXXXXX designate the sequences complementary to 5'-terminal sequences of a target RNA, and the 3'-terminal two nucleotides are RNAs. For subsequent Rn12 ligation, the target RNA in 3'- or 5'-Db-PCR should contain a 3'-OH or 5'-P end, respectively. If the target RNA is expected to contain a different terminal structure, total RNA should be subjected to dephosphorylation/phosphorylation treatment in advance. If the hybridized RNA is the target RNA with exact terminal sequences, the hybridization unites the Db-adapters and the target RNA to form double-stranded nucleotides containing a nick, which is an efficient substrate for Rn12 ligation (40-42). Following hybridization, Rn12 ligates the adapter to the target RNA to generate a ligation product with a one-sided "dumbbell-like" secondary structure. Rn12 ligation efficiency becomes severely reduced when double-stranded nucleotides of the substrate contain gaps or overlaps (41), suggesting that Rn12 ligation achieves high specificity toward target RNA.

Figure 1C:
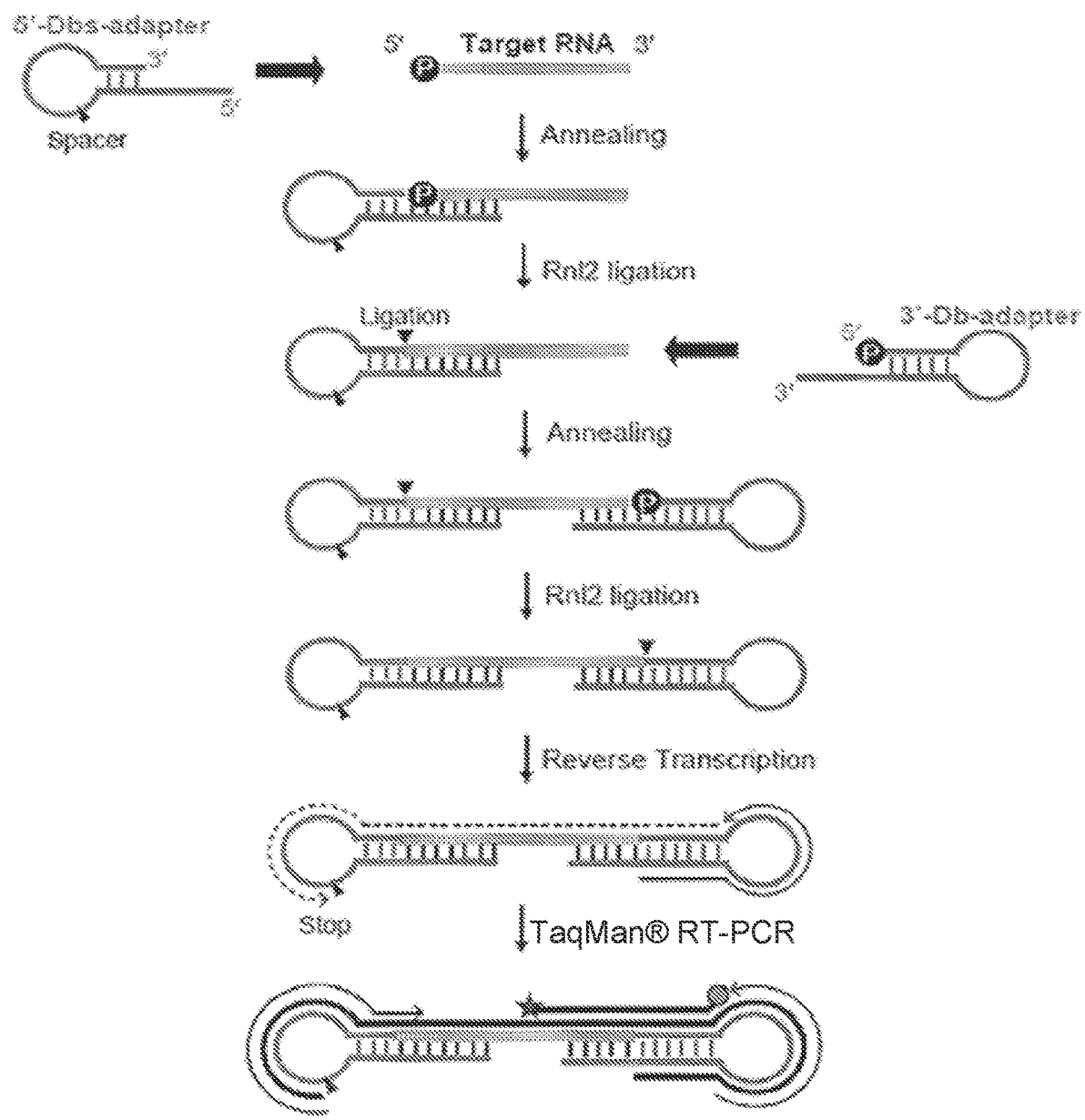
FIG. 1(C) depicts a schematic representation of Db-PCR.

Finally, the ligation product is amplified and quantified by TaqMan® RT-PCR. The TaqMan® probe is designed to target the boundary of the adapter and target RNA for the PCR to exclusively quantify "dumbbell-like" ligation products. Because a half part of the TaqMan® probe recognizes the adapter and the rest half part recognizes target RNAs (each part being a boundary), the TaqMan® probe thereby targeting the "boundary of the adapter and target RNAs", the TaqMan® probe specifically quantifies "adapter-target RNA ligation product" without any cross-reaction from unligated adapter or RNAs. Because the TaqMan® probe has the ability to discriminate difference of a single nucleotide (47), the design results in highly specific detection of target RNA, which does not cross-react with its 3'- or 5'-terminal variants. Hence, 3'- or 5'-Db-PCR results in highly specific detection and quantification of specific 3'- or 5'-variant of RNAs with single-nucleotide discrimination ability. These two methods can be further combined to design a Dumbbell PCR (Db-PCR) method for selective quantification of a specific variant of small RNAs to simultaneously discriminate target RNAs from their corresponding 5'- and 3'-variants (FIG. 1C).

Figure 4A:
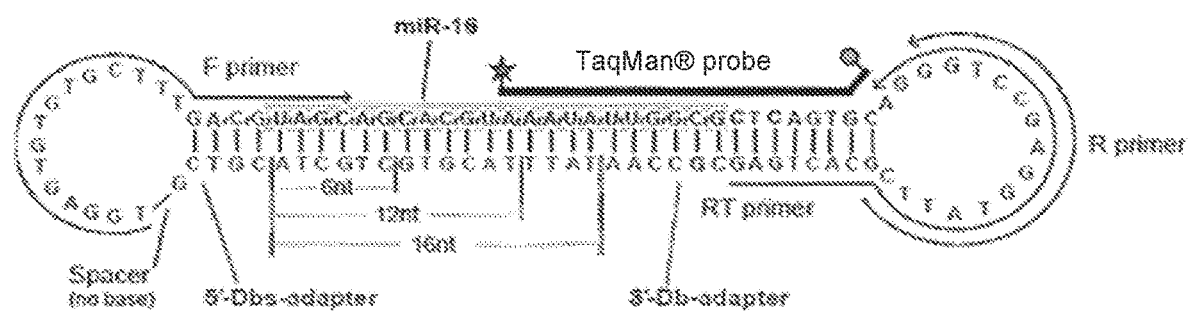
FIG. 4(A) depicts the formation of the stem-loop structure of both a 3'-Db-adapter whose protruding 3'-end base-pairs with the 3'-end of target RNA and 5'-Db-adapter whose protruding 5'-end base-pairs with the 3'-end of target RNA and (i) the F primer is shown in SEQ ID NO: 43, (ii) the R primer is shown in SEQ ID NO: 13, (iii) the 3'-Db-adapter is shown in SEQ ID NO: 42, (iv) the 5'-Dbs-adapter is shown in SEQ ID NO: 41, (v) the RT primer is shown in SEQ ID NO: 12, (vi) the TaqMan® probe is shown in SEQ ID NO: 44, and (vii) the miR-16 is shown in SEQ ID NO: 5.

For amplification by Db-PCR, target RNA should contain the both 5'-P and 3'-OH ends. Db-PCR utilizes a 5'-Dbs-adapter (5'-Dumbbell adapter with spacer) which was designed to contain a base-lacking 1', 2'-dideoxyribose spacer in the loop region. The 5'-Dbs-adapter contains both DNA and RNA and forms a stem-loop structure with 16 nucleotides protruding from the 5'-end (FIG. 4A). Its sequences are "5'-XXXXXXXXXXXXXXXX CGTCG/idSp/TGGAGTGTGTGCTTTGArCrG (SEQ ID NO: 3)". The 5'-terminal 16 nucleotides XXXXXXXXXXXXXXXX designate the sequences complementary to 5'-terminal sequences of a target RNA, and idSp designates a base-lacking spacer. Db-PCR procedure involves hybridization and Rn12 ligation of the 5'-Dbs-adapter to the 5'-end of target RNAs, followed by 3'-Db-adapter (SEQ ID NO: 1) addition and ligation to the 3'-end. After generating the "dumbbell-like" ligation product, reverse transcription is performed to synthesize cDNAs from the 3'-Db-adapter region. The reaction terminates at the nucleotide preceding a spacer in the loop region of the 5'-Dbs-adapter, which prevents the reaction from continuing to the end of the 5'-adapter and thus generating highly structured cDNAs, which may impair subsequent PCR steps. Subsequent TaqMan® PCR is used to quantify the generated cDNAs. TaqMan® probes are designed to target the boundary of the target RNA and 3'-Db-adapter. The forward primer is derived from the 5'-Dbs-adapter with a few 3'-terminal nucleotides corresponding to 5'-end of the target RNA, whereas the reverse primer is derived from the 3'-Db-adapter. These designs render PCR amplification completely dependent on ligation of both the 5'- and 3'-adapters to exclusively amplify "dumbbell-like" ligation products. In addition, both 5'- and 3'-terminal sequences are assured by the forward primer and TaqMan® probe. Hence, Db-PCR governs highly specific detection and quantification with single nucleotide discrimination ability at both the 5'- and 3'-terminal sequences of target RNAs.

Discriminative Quantification of Small RNAs and their 3'-Variants by 3'-Db-PCR

Figure 7:
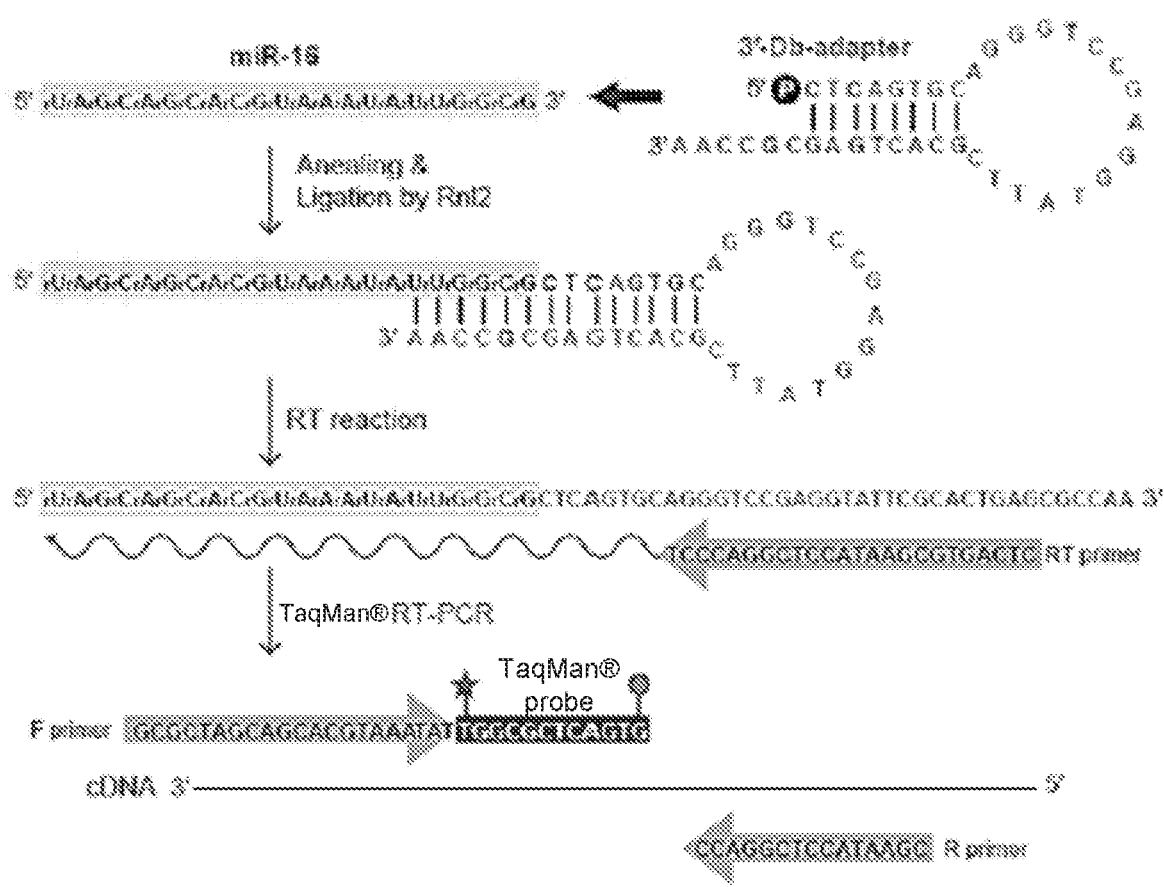
FIG. 7 depicts a schematic representation of the quantification of miR-16 by 3'-Db-PCR and (i) the 3'-Db-adapter is shown in SEQ ID NO: 18, (ii) the miR-16 is shown in SEQ ID NO: 5, (iii) the RT reaction is shown in SEQ ID NO: 5 and SEQ ID NO: 18, and the RT primer is shown in SEQ ID NO: 12, (iv) the R primer is shown in SEQ ID NO: 13, (v) the TaqMan® probe is shown in SEQ ID NO: 21, and (vi) the F primer is shown in SEQ ID NO: 20.

The 3'-Db-PCR scheme was evaluated by targeting human miR-16, a widely expressed miRNA in tissues and cells (48) (FIG. 7). The 3'-Db-adapter is composed of DNA with 5'-P and 3'-OH termini, which forms a stem-loop structure containing loop sequences that are identical to those of the stem-loop primer for the standard miRNA quantification method (37) and a protruding 3'-end complementary to the 5'-end of the target RNA (FIGS. 2A, 7).

Figure 8:
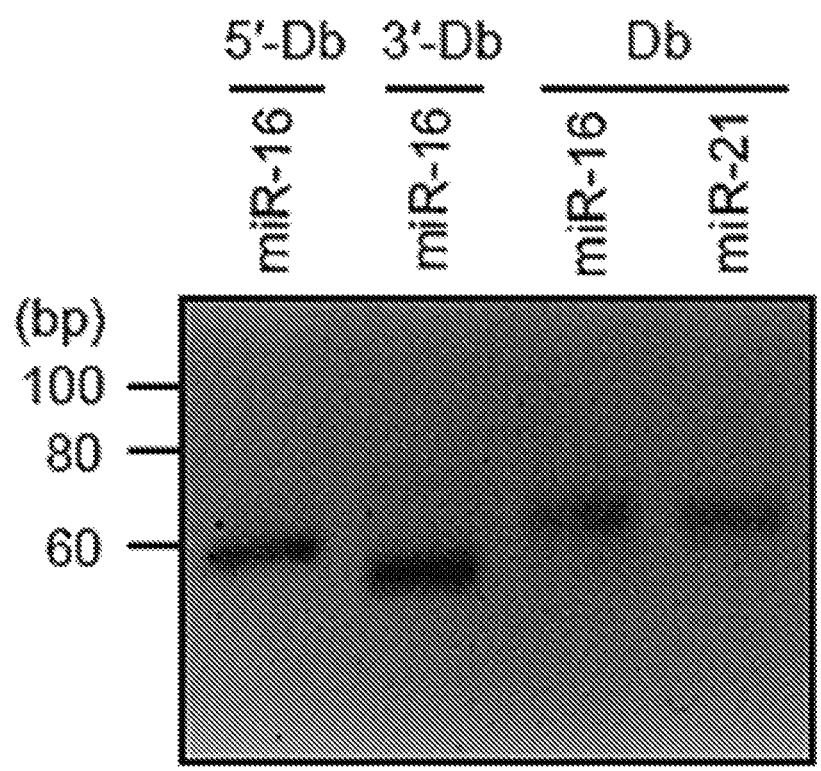
FIG. 8 depicts 5'-Db-PCR, 3'-Db-PCR, and Db-PCR amplified cDNAs as a clear band.

The hybridization of the 3'-Db-adapter with the target RNA forms double-stranded DNA/RNA hybrids containing a nick of "RNA-OH-3'/5'-P-DNA", which is an efficient substrate for Rn12 ligation (40-42). The 3'-Db-PCR procedure successfully amplified synthetic miR-16 (data not shown) and endogenous miR-16 in total RNA from HeLa cells as a single amplified band (FIG. 8).

Figure 2B:
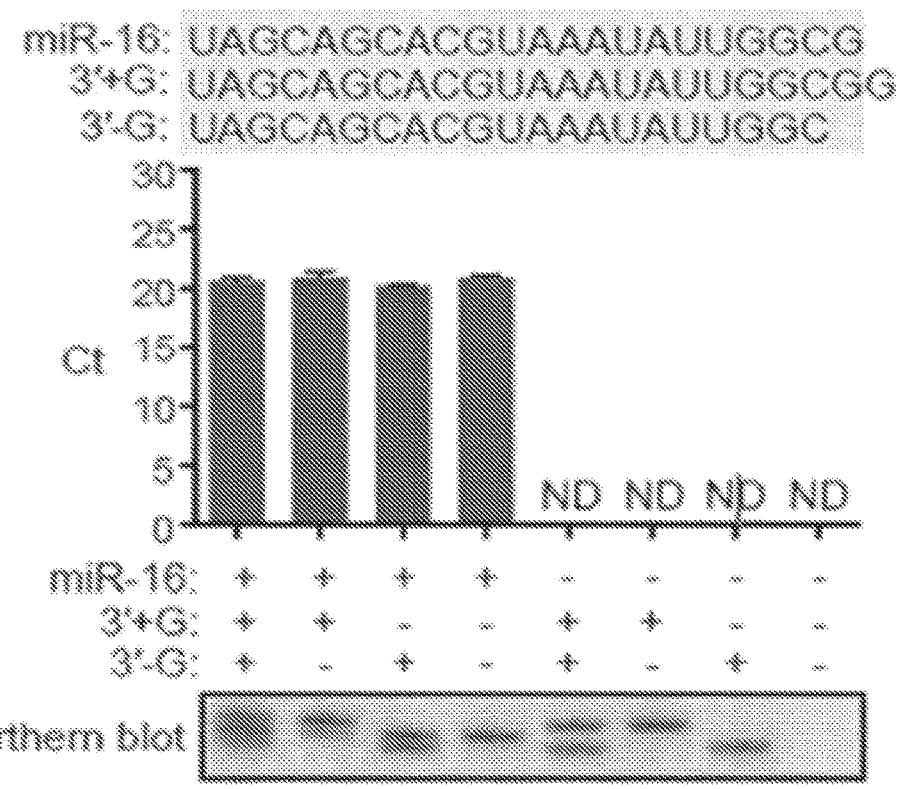
FIG. 2(B) illustrates the specificity of 3'-Db-PCR to quantify specific 3'-variants of small RNAs and (i) the miR-16 is shown in SEQ ID NO: 5, (ii) the 3'+G is shown in SEQ ID NO: 7, and (iii) the 3'−G is shown in SEQ ID NO: 8.
Figure 9A:
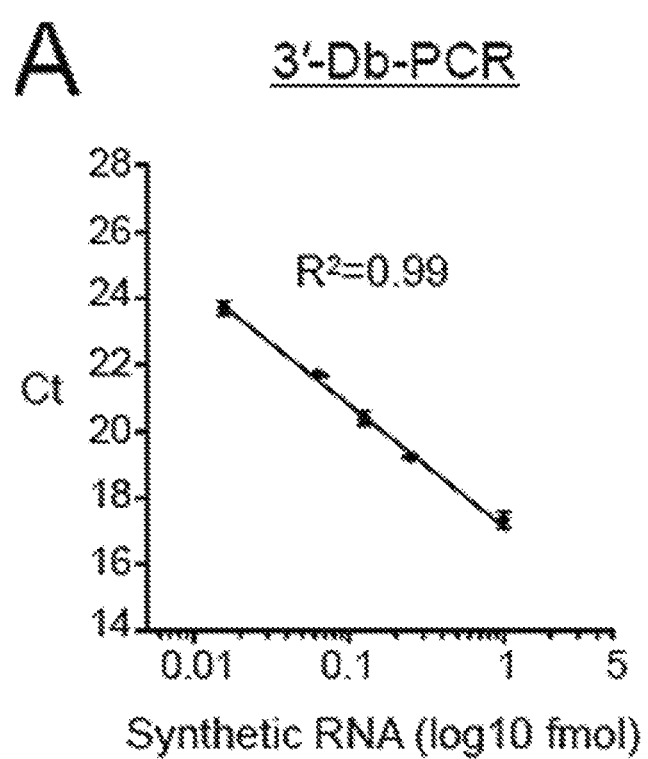
FIG. 9(A) depicts proportional correlation of miR-16 input to the Ct value obtained by 3'Db-PCR.

The ability of the 3'-Db-PCR to discriminate target RNA from its variants that differ in sequences by a minimum of a single nucleotide was tested with the two 3'-variants containing an additional G (miR-16-[3'+G]) or lacking a G (miR-16-[3'–G]). As shown in FIG. 2B, neither of the variants produced a detectable signal by 3'-Db-PCR specifically designed for authentic miR-16. Furthermore, the Ct value from miR-16 was nearly equal to those from the mixtures of miR-16 and its 3'-variants. These results indicate that 3'-Db-PCR specifically and exclusively quantifies authentic miR-16 without cross-reactivity to coexisting 3'-variants. To examine the quantification ability, 3'-Db-PCR was applied for different amounts of synthetic miR-16 (0.01-1 fmol). The quantifications showed clear linearity between the log of miR-16 input and Ct value (FIG. 9A), indicating that the 3'-Db-PCR method has a dynamic range of at least two orders of magnitude and is capable of quantifying synthetic target RNA.

Figure 2C:
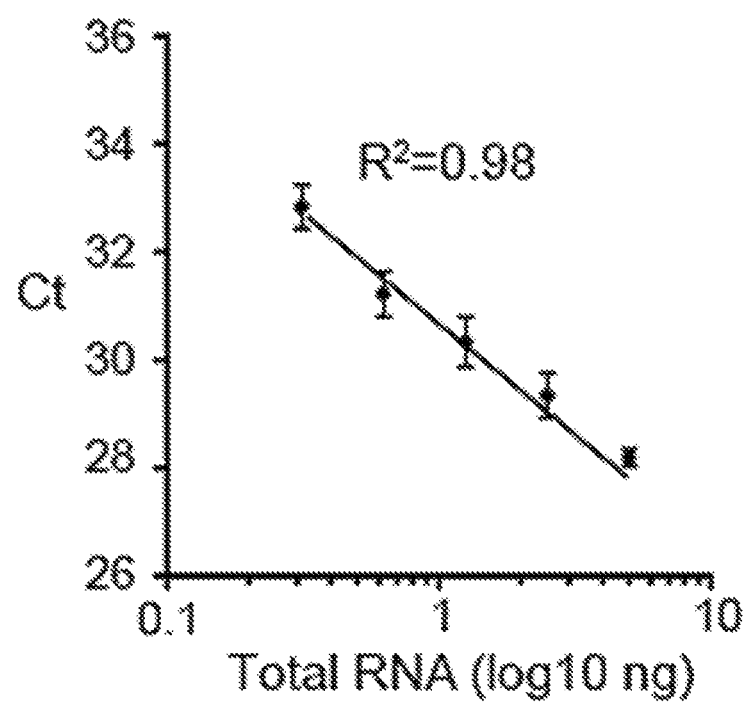
FIG. 2(C) illustrates the linearity between total RNA input and detected CT value.

These methods were further used to quantify endogenous miR-16 in HeLa total RNA (0.5-5 ng). The results showed excellent linearity between total RNA input and detected Ct value (FIG. 2C), indicating the capability of 3'-Db-PCR to quantify endogenous target RNA in total RNA.

To further examine the discriminative ability of 3'-Db-PCR, the method for quantification of *Bombyx mori* piRNAs and their 3'-variants expressed in BmN4 cells was examined. BmN4 cells are *B. mori* ovary-derived cultured germ cells that endogenously express 24-30-nt piRNAs and their bound PIWI proteins, both of which play crucial roles in germline development, and therefore are a unique model system for piRNA research (49). In prior studies, BmPAPI was identified as a piRNA biogenesis factor shaping the 3'-end maturation step of piRNAs and determined that BmPAPI-depletion causes 3'-terminal extension of mature piRNAs in BmN4 cells (45).

Figure 2D:
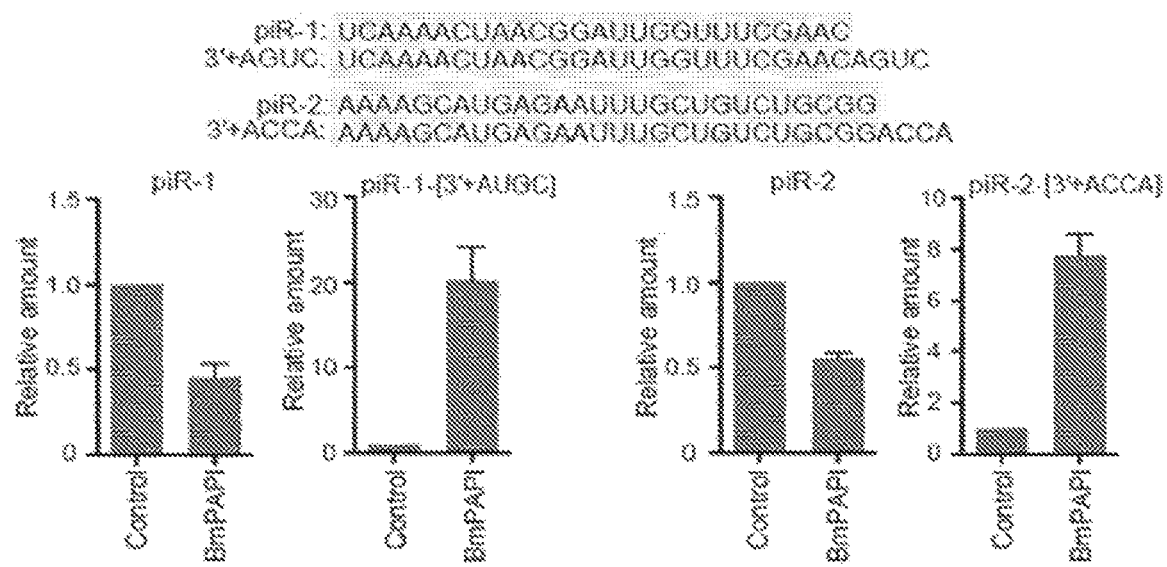
FIG. 2(D) demonstrates the capability of 3'-Db-PCR for discriminate quantification of small RNAs and their endogenous 3'-variants and (i) the piR-1 is shown in SEQ ID NO: 54, (ii) the 3'+AGUC is shown in SEQ ID NO: 55, (iii) the piR-2 is shown in SEQ ID NO: 56, and (iv) the 3'+ACCA is shown in SEQ ID NO: 57.

Accordingly 3'-Db-adapters and primers were designed for two BmN4-expressing mature piRNAs, piR-1 and piR-2, and their 3'-variants containing four additional nucleotides, piR-1-[3'+AGUC] and piR-2-[3'+ACCA], whose expression levels were expected to be enhanced upon BmPAPI-depletion (FIG. 10) (45). 3'-Db-PCR quantifications were then performed using total RNA extracted from BmN4 cells treated with control or BmPAPI-targeted dsRNAs. As a result, BmPAPI depletion commonly reduced piR-1 and piR-2 levels, whereas the levels of piR-1-[3'+AGUC] and piR-2-[3'+ACCA] were markedly upregulated (FIG. 2D). Thus, 3'-Db-PCR quantification allowed for discriminate quantification of small RNAs and their endogenous 3'-variants, which recapitulated our previous findings, showing the credibility and general versatility of the method to quantify specific 3'-variants of small RNAs.

Discriminative Quantification of miRNAs and their 5'-Variants by 5'-Db-PCR

Figure 3B:
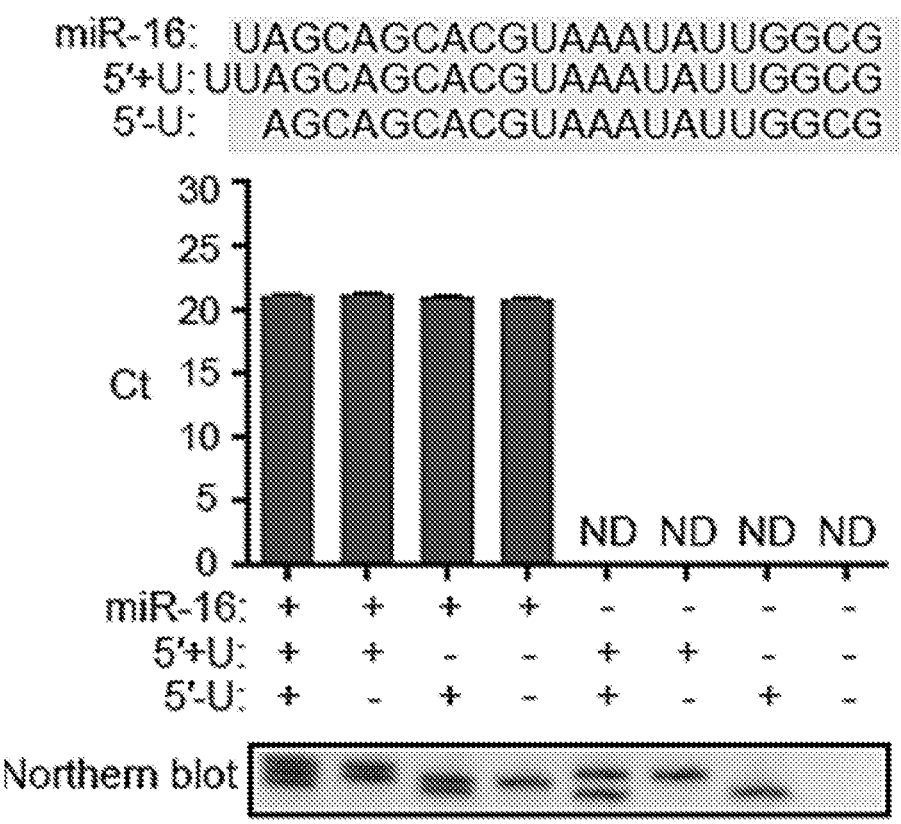
FIG. 3(B) illustrates the specificity of 5'-Db-PCR to quantify specific 5'-variants of small RNAs and (i) the miR-16 is shown in SEQ ID NO: 5, (ii) the 5'+G is shown in SEQ ID NO: 6, and (iii) the 5'−G is shown in SEQ ID NO: 58.
Figure 11:
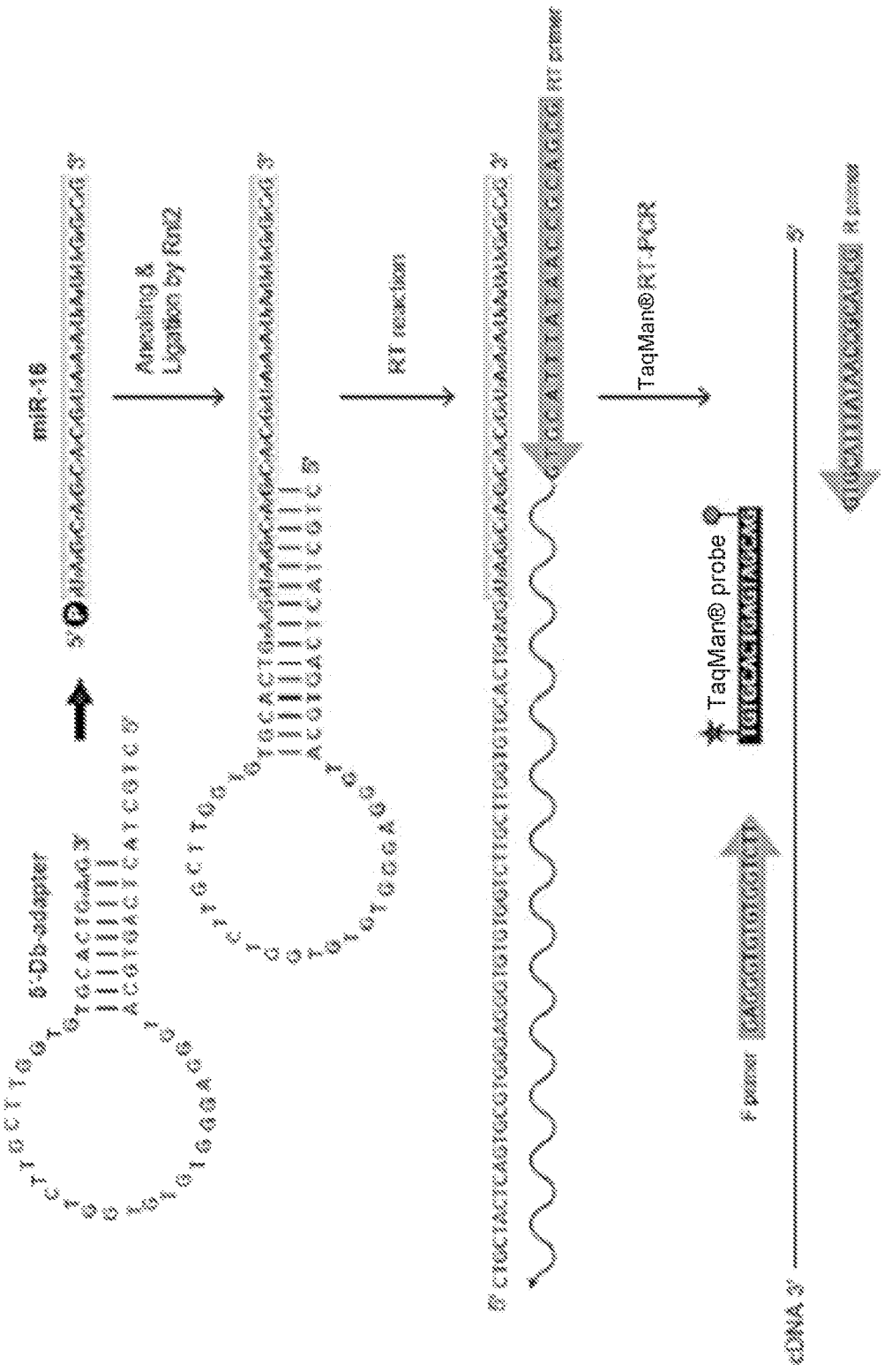
FIG. 11 depicts a schematic representation of the quantification of miR-16 by 5'-Db-PCR and (i) the 5'-Db-adapter is shown in SEQ ID NO: 32, (ii) the miR-16 is shown in SEQ ID NO: 5, (iii) the RT reaction is shown in SEQ ID NO: 32 and SEQ ID NO: 5, and the RT primer is shown in SEQ ID NO: 33, (iv) the F primer is shown in SEQ ID NO: 14, (v) the TaqMan® probe is shown in SEQ ID NO: 34, and (vi) the R primer is shown in SEQ ID NO: 33.

Human miR-16 was targeted again to evaluate the 5'-Db-PCR scheme (FIG. 11). The stem-loop 5'-Db-adapter contains both 5'- and 3'-OH ends and is composed of DNA except for the last two 3'-terminal nucleotides that are designed as RNA (FIG. 3A, 11). Therefore, the hybridization of the 5'-Db-adapter with the target RNA generates double-stranded DNA/RNA hybrids containing a nick of "RNA-OH-3'/5'-P-RNA" between the 3'-end of the adapter and 5'-end of the target, which is an efficient substrate for Rn12 ligation (40-42). The 5'-Db-PCR method successfully amplified synthetic miR-16 (data not shown) and HeLa endogenous miR-16 as a single band (FIG. 8). Both synthetic 5'-variants of miR-16, containing an additional U (miR-16-[5'+U]) or lacking a U (miR-16-[5'–U]) failed to show detectable signals, and the Ct value obtained from miR-16 was identical to those from the mixtures of miR-16 and its 5'-variants (FIG. 3B).

Figure 3C:
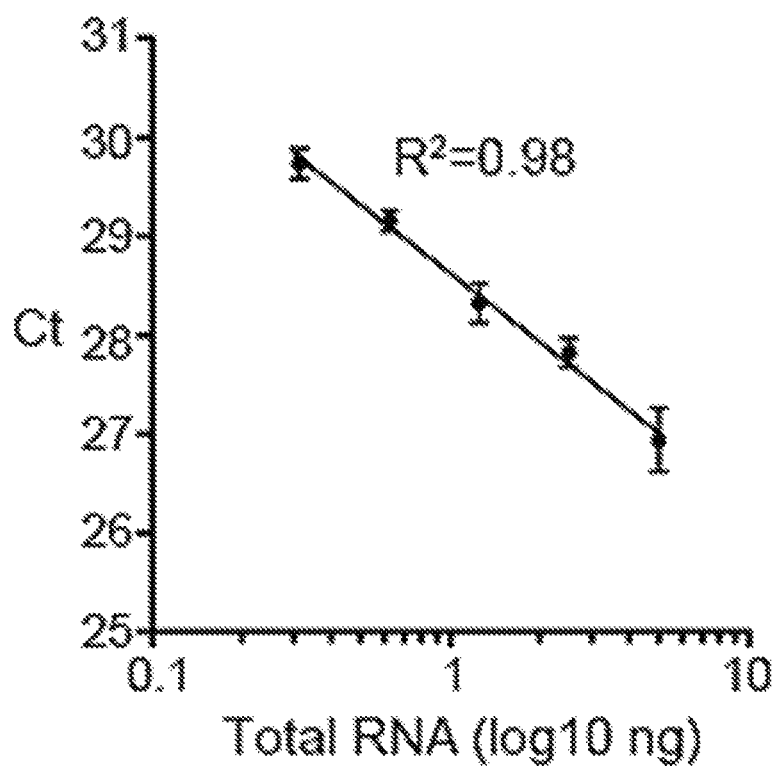
FIG. 3(C) illustrates the linearity between total RNA input and detected CT value.
Figure 9B:
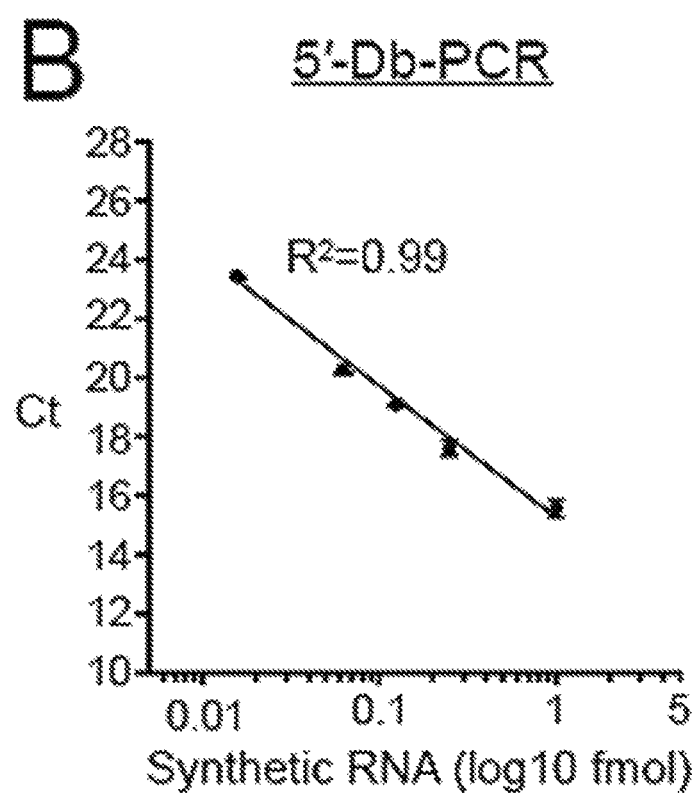
FIG. 9(B) depicts proportional correlation of miR-16 input to the Ct value obtained by 5'-Db-PCR.
Figure 12:
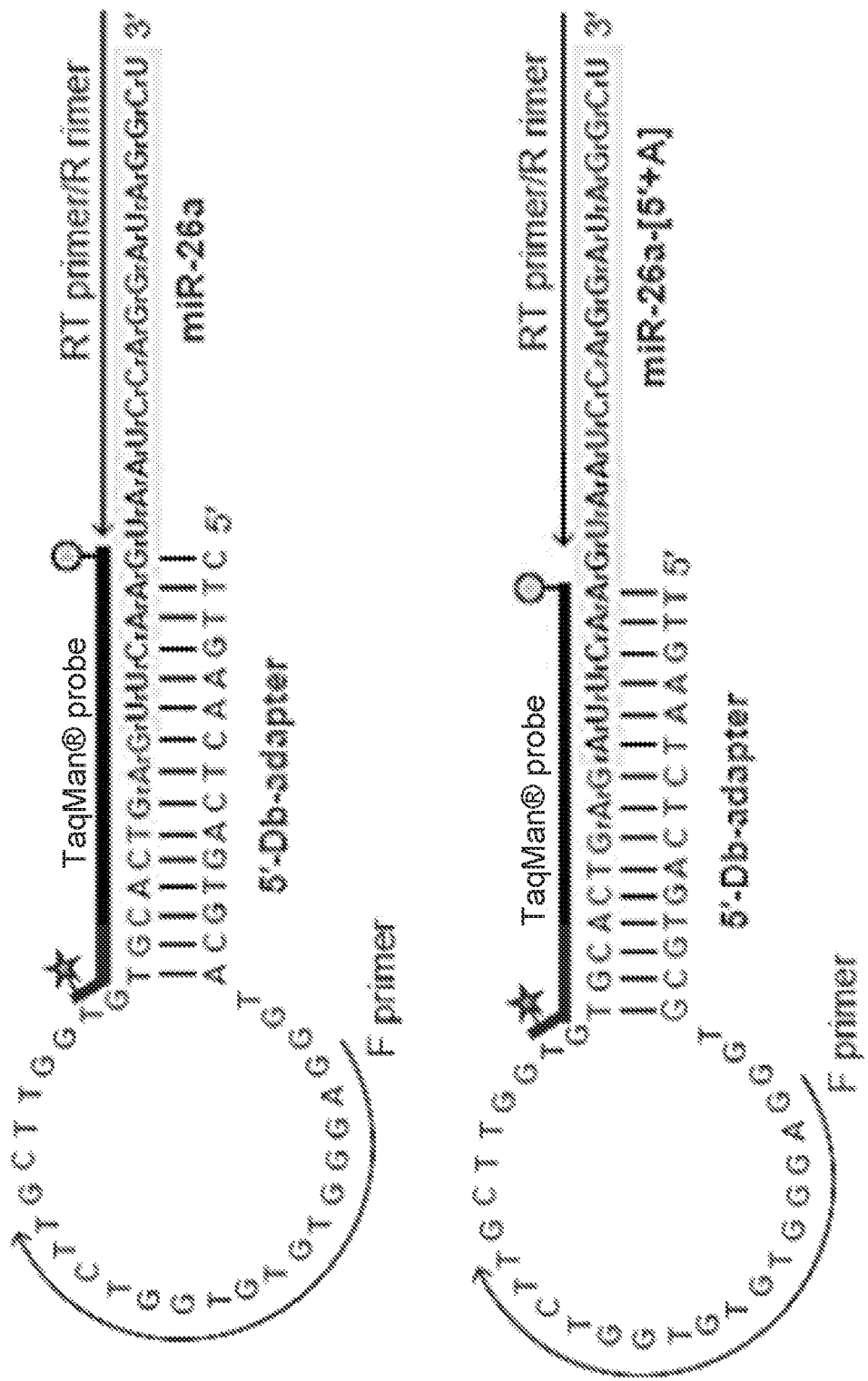
FIG. 12 depicts sequences and secondary structures of the 5'-Db-adapter and targeted human microRNAs quantified by 5'-Db-PCR and the 5'-Db-adapters are shown, from top to bottom, in (i) SEQ ID NO: 66 and (ii) SEQ ID NO:38 and the miR RNAs are shown, from top to bottom, in (i) SEQ ID NO: 59; and (ii) SEQ ID NO: 60. The regions of the miR targets and 5'-Db-adapter targeted by the F primer, the RT/R primer, and the probe can be seen in FIG. 12.

These results indicate that 5'-Db-PCR exclusively quantifies authentic miR-16 with the single-nucleotide resolution at 5'-terminal sequences. Clear linearity between the sample input and Ct value was observed for 5'-Db-PCR using different amounts of synthetic miR-16 (FIG. 9B) and HeLa total RNA (FIG. 3C), indicating the quantification ability of 5'-Db-PCR for endogenous target RNAs as well as synthetic RNAs. To further test the credibility and applicability of 5'-Db-PCR, we targeted human miR-26a and miR-26a45'±A], a 5'-isomiR of miR-26a containing an additional A residue (FIG. 12).

Tan et al (32) has recently reported that HepG2 cells express both miR-26a and miR-26a-[5'-hA], although expression of miR-26a45'±A] was much lower compared to that of miR-26a. According to Northern blot analyses, HEK293 cells also expressed miR-26a and miR-26a-[5'+A]. Compared to HepG2 expression, HEK293 expression of both miRNAs seemed much lower, but there was little difference in relative expression levels of miR-26a and miR-26a-[5'+A]. HeLa cells showed an only faint band on Northern blot analysis of miR-26a, and no band was detected for miR-26a-[5'+A] (32). Accordingly, in this study 5'-Db-PCR was applied to quantify the two miRNAs in total RNA from HepG2, HEK293, and HeLa cell lines. As shown in FIG. 2E, both miR-26a and miR-26a45'±A] were successfully amplified by 5'-Db-PCR from HepG2 cells with Ct values of 26.55±0.27 and 30.10±0.27, respectively, suggesting that 5'-Db-PCR distinctively amplified miR-26a and its much less-abundant 5'-isomiR. Relative amounts of miR-26a and miR-26a45'±A] in HEK293 cells versus those in HepG2 cells were revealed to be 0.145±0.004 and 0.166±0.011, respectively. miR-26a was quantified by 5'-Db-PCR at much lower amounts in HeLa cells than in the other two cell lines, whereas miR-26a-[5'+A] expression was undetectable in HeLa cells. These results well recapitulated those of a previous report (32).

Discriminative Quantification of miR-16 and its Variants by Dumbbell PCR

Figure 4B:
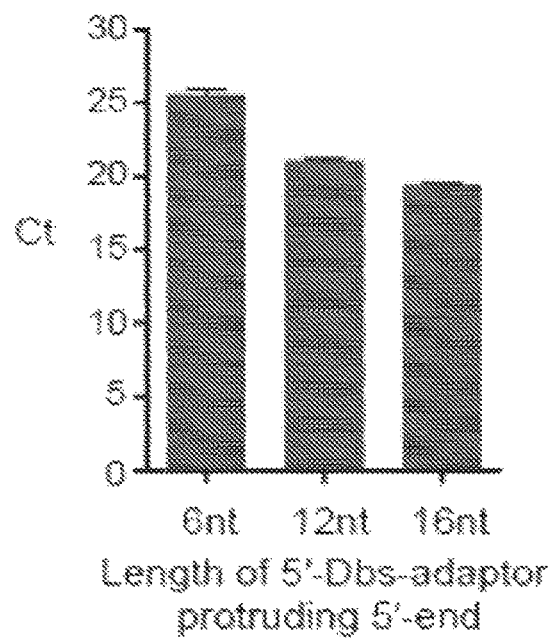
FIG. 4(B) demonstrates that the longer protruding 5'-end resulted in more efficient detection.
Figure 13:
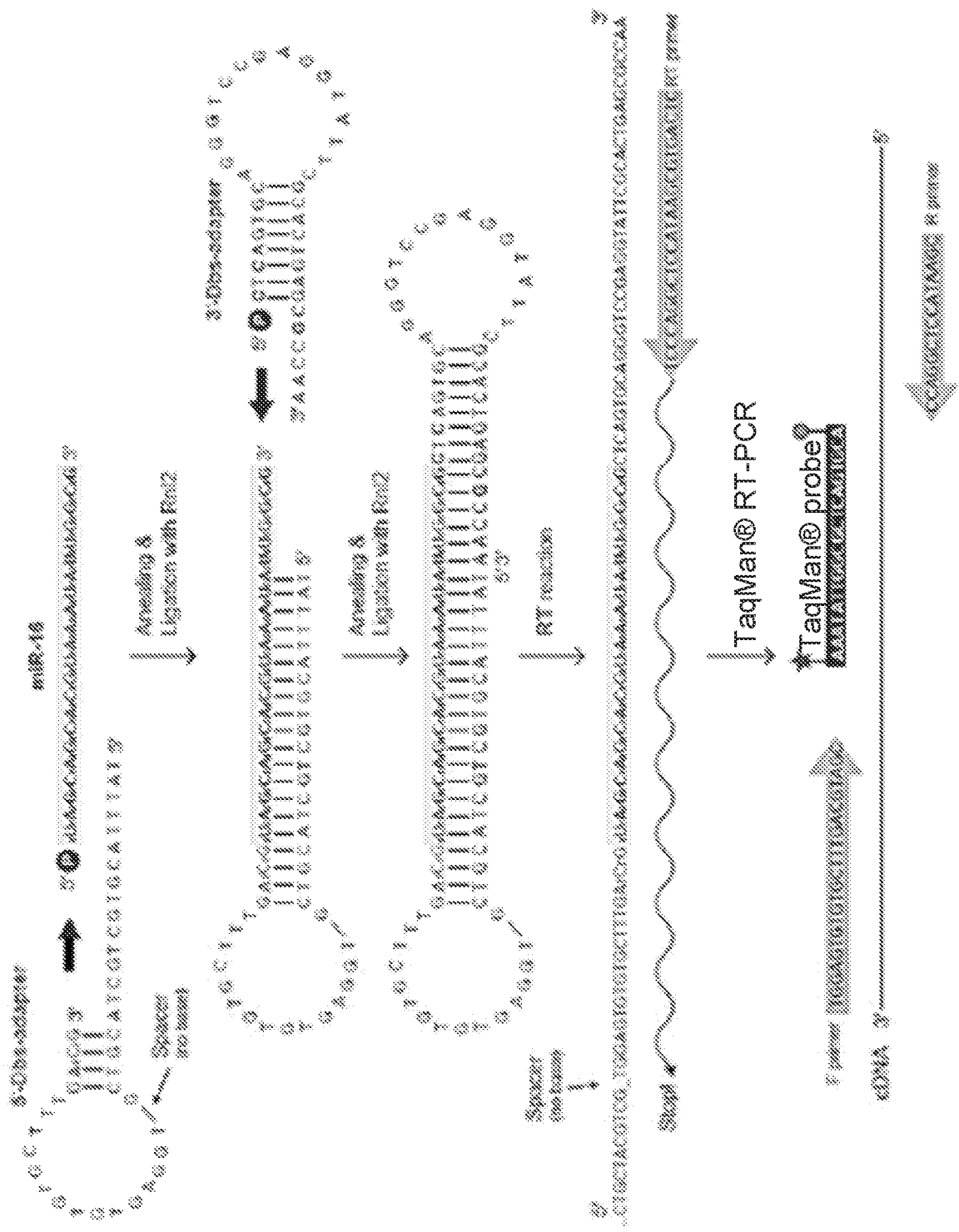
FIG. 13 depicts a schematic representation of the quantification of miR-16 by Db-PCR and from top to bottom (i) the 5'-Dbs-adapter is shown in SEQ ID NO: 41, (ii) the miR-16 is shown in SEQ ID NO: 5, (iii) the 3'-Dbs-adapter is shown in SEQ ID NO: 18, (iv) the RT reaction is shown in SEQ ID NO: 41, SEQ ID NO: 5, and SEQ ID NO: 18, and the RT primer is shown in SEQ ID NO: 12, (v) the F primer is shown in SEQ ID NO: 43, (vi) the TaqMan® probe is shown in SEQ ID NO: 44, and (vii) the R primer is shown in SEQ ID NO: 13.

Because both 5'- and 3'-Db-PCRs showed high specificity with single nucleotide resolution and quantification ability, we further evaluated the Db-PCR scheme, which was designed by combining the two methods, by targeting human miR-16 (FIG. 13). Db-PCR utilizes a stem-loop 5'-Dbs-adapter containing a base-lacking spacer in the loop region and the 3'-Db-adapter used in 3'-Db-PCR (FIG. 4A, 13). In the process of identifying effective 5'-Dbs-adapter constructs, the length of the protruding 5'-end was found to affect detection efficiency. Three different 5'-Dbs-adapters containing 6, 12, or 16 nucleotides protruding from the 5'-end were used. As shown in FIG. 4B, the longer protruding 5'-end resulted in more efficient detection, which was most likely due to the high stability of the adapter-target RNA duplex. Thus, the 5'-Dbs-adapter with a 16-nt protruding end was used in the subsequent experiments.

Figure 4C:
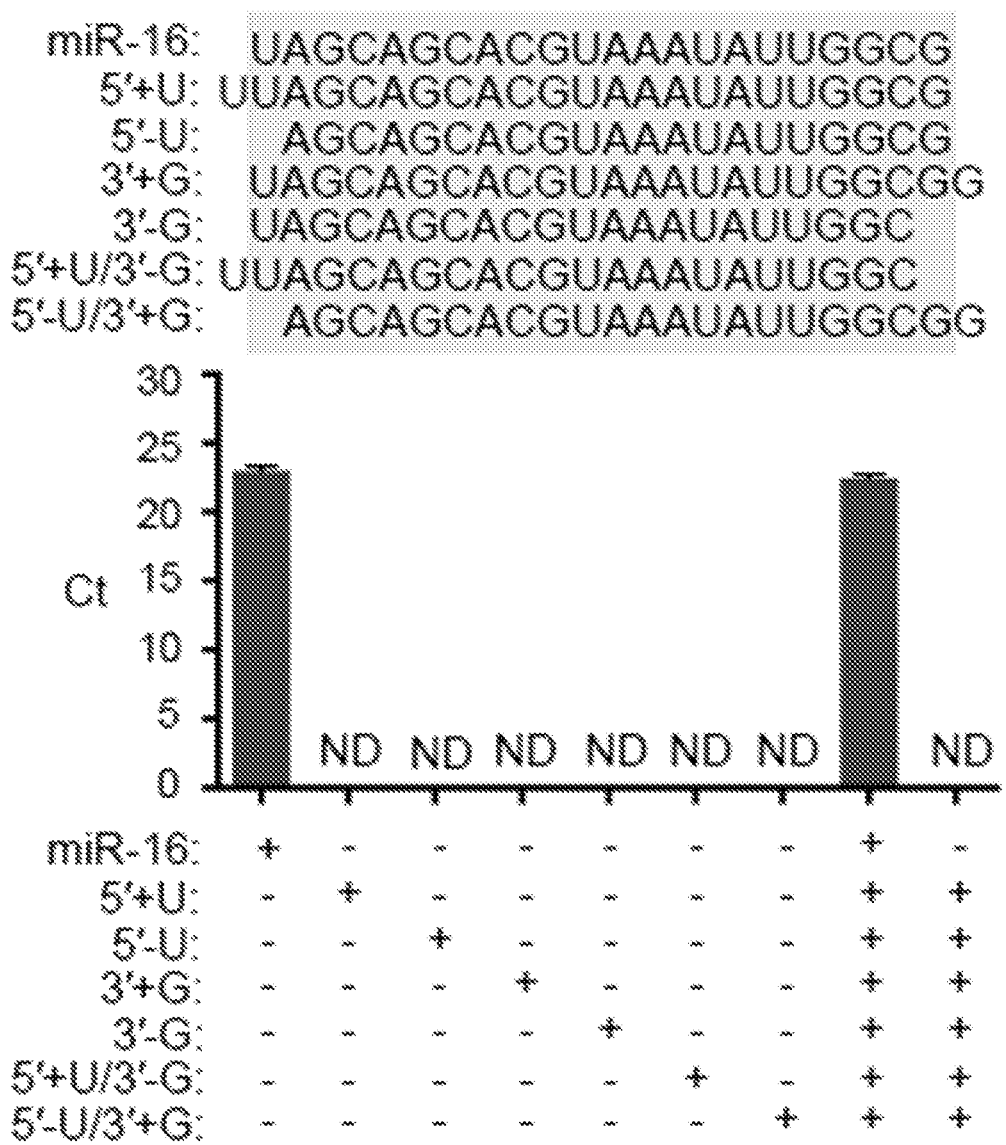
FIG. 4(C) illustrates that all tested 5'-variants and 3'-variants and their combinatorial variants containing an additional nucleotide or lacking a nucleotide at their termini failed to show detectable signals and (i) the miR-16 is shown in SEQ ID NO: 5, (ii) the 5'+U is shown in SEQ ID NO: 6, (iii) the 5'−U is shown in SEQ ID NO: 61, (iv) the 3'+G is shown in SEQ ID NO: 7, (v) the 3'−G is shown in SEQ ID NO: 8, (vi) the 5'+U/3'−G is shown in SEQ ID NO: 9, and (vi) the 5'+U/3'+G is shown in SEQ ID NO: 10.
Figure 4D:
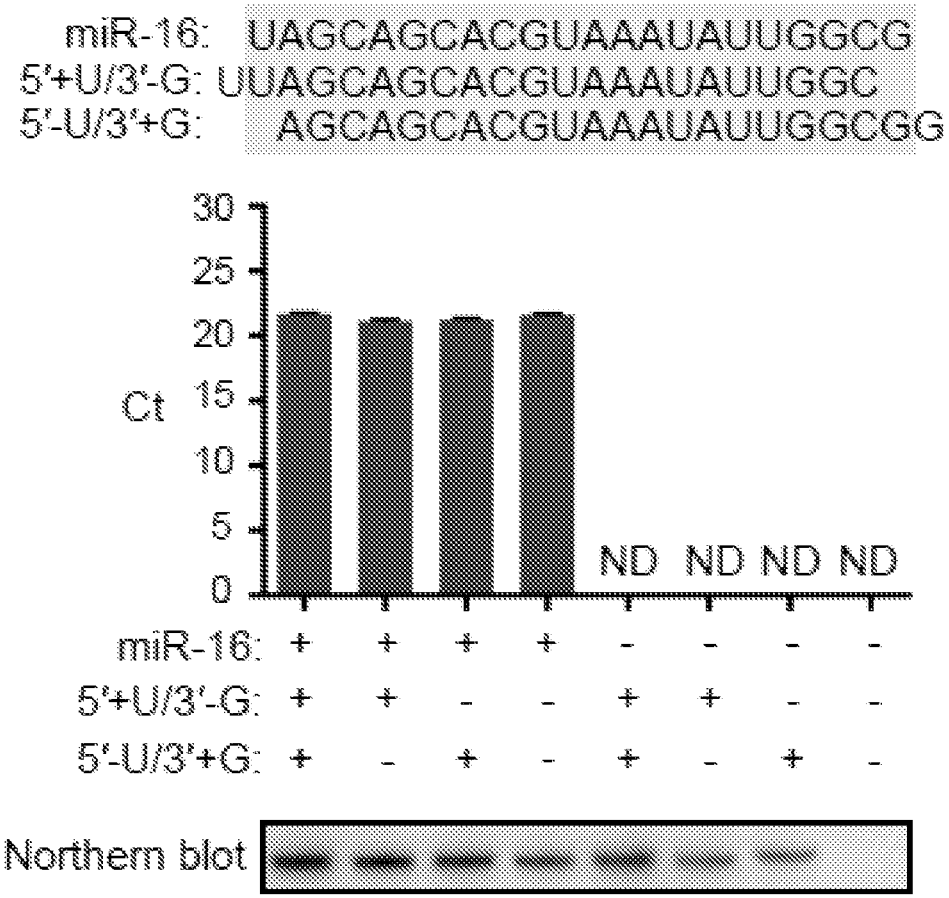
FIG. 4(D) illustrates the high specificity of Db-PCR and (i) the miR-16 is shown in SEQ ID NO: 5, (ii) the 5'+U/3'−G is shown in SEQ ID NO: 6, and (iii) the 5'−U/3'+G is shown in SEQ ID NO: 10.
Figure 4E:
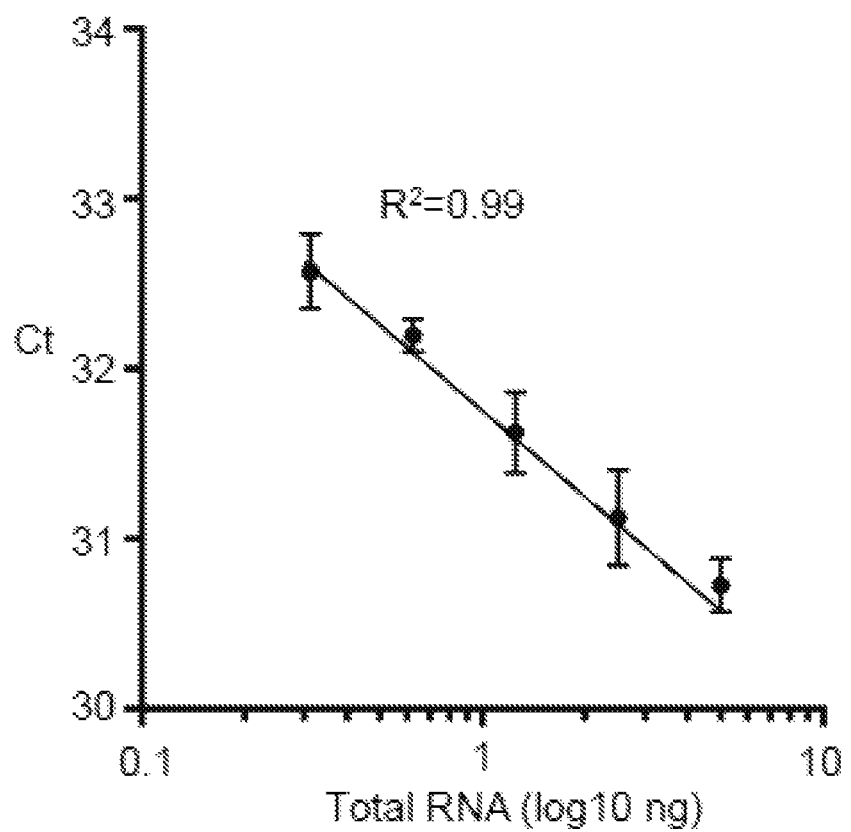
FIG. 4(E) demonstrates Db-PCR applied to endogenous miR-16 in HeLa total RNA.
Figure 9C:
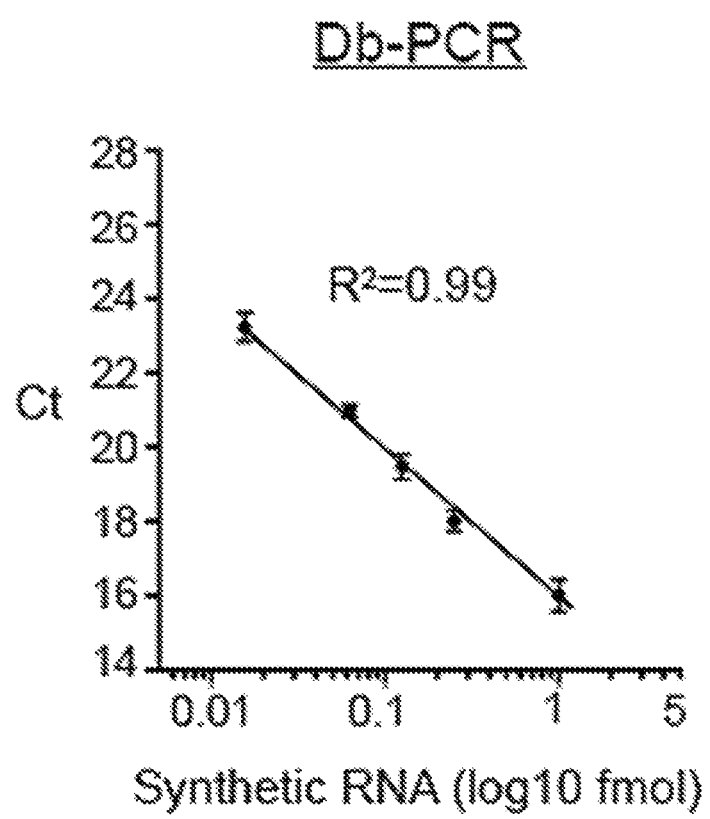
FIG. 9(C) depicts proportional correlation of miR-16 input to the Ct value obtained by Db-PCR.

Db-PCR successfully amplified synthetic miR-16 (data not shown) and endogenous miR-16 in HeLa total RNA as a single amplified band (FIG. 8). As shown in FIG. 4C, all tested 5'- and 3'-variants and their combinatorial variants containing an additional nucleotide or lacking a nucleotide at their termini failed to show detectable signals. In addition, the Ct value obtained from miR-16 alone was nearly equal to those from the mixture of miR-16 and six of its variants, indicating the high specificity of the method toward authentic target RNAs with single-nucleotide resolution at both the 5'- and 3'-terminal sequences. While two of the variants, miR-16-[5'+U/3'−U] and miR-16-[5'−U/3'+U], have the same length with miR-16 and were thus indistinguishable from miR-16 by Northern blot, Db-PCR exclusively detected authentic miR-16 (FIG. 4D), confirming the high specificity of the Db-PCR toward authentic target RNA, which is not available by Northern blot. Db-PCR was further applied for different amounts of synthetic miR-16 (FIG. 9C) and endogenous miR-16 in HeLa total RNA (FIG. 4E). Both cases showed linearity between the log of sample input and Ct value, indicating the capability of Db-PCR to accurately reflect the relative amount of target RNA in total RNA.

Figure 5A:
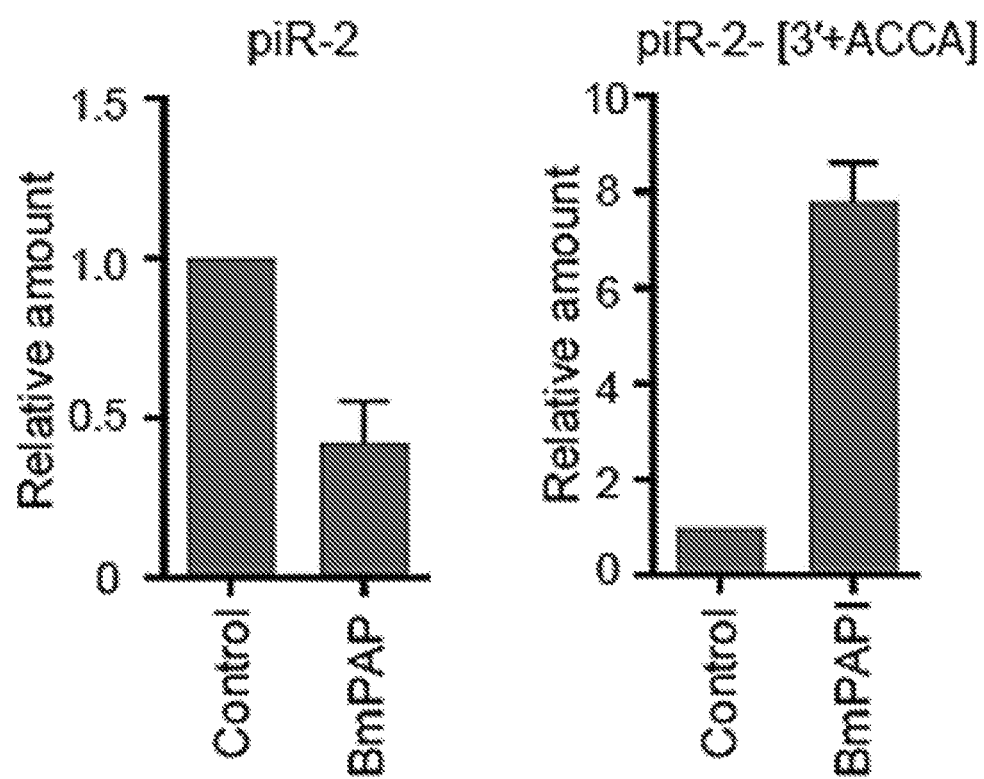
FIG. 5(A) depicts small RNA quantifications by Db-PCR in BmN4 and human cancer cell lines.
Figure 5B:
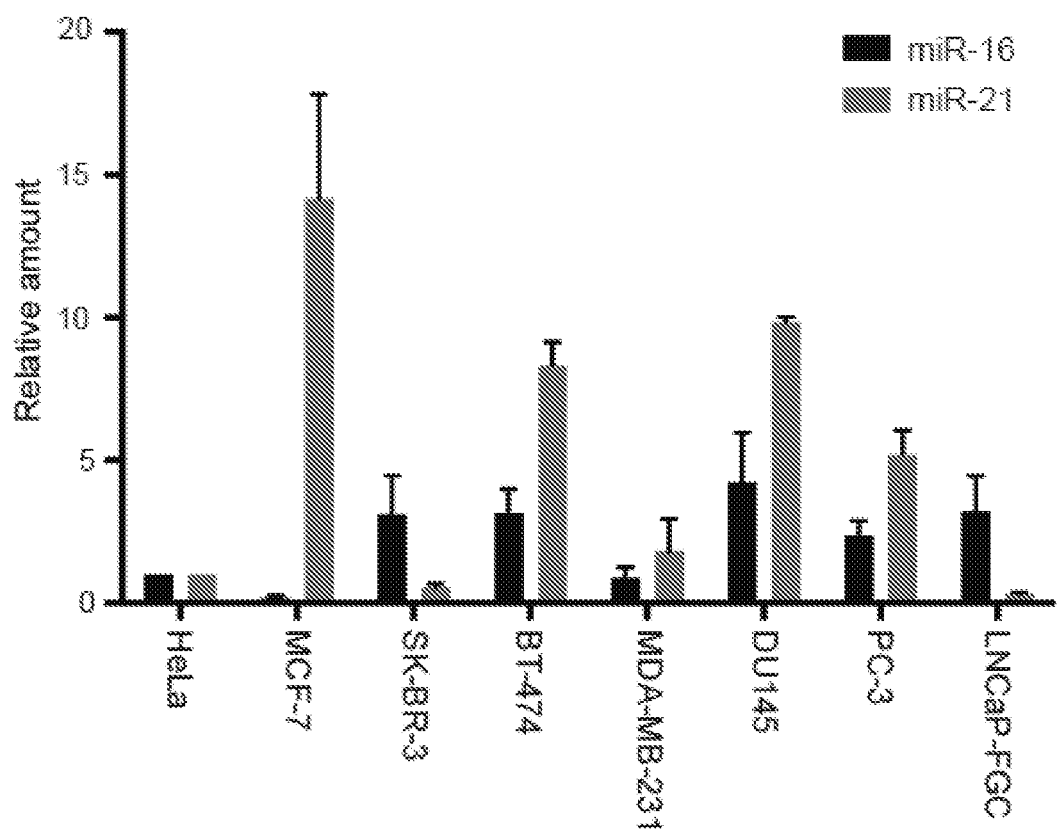
FIG. 5(B) demonstrates application of Db-PCR determine expression profiles of miR-16 and miR-21 from eight different human cancer cell lines.
Figure 14:
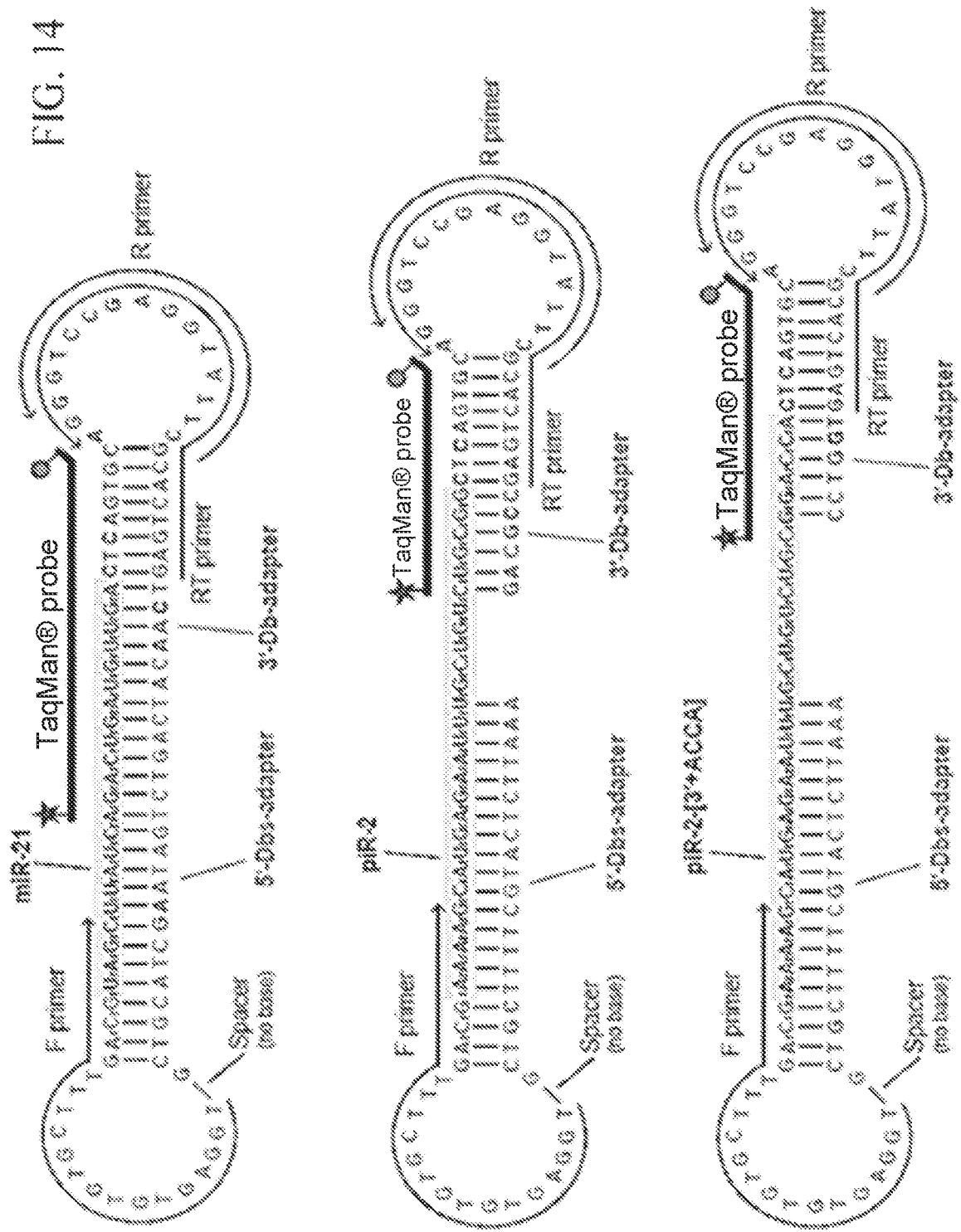
FIG. 14 depicts sequences and secondary structures of the adapters and targeted small RNAs quantified by Db-PCR and from top to bottom (i) the miR-21 is shown in SEQ ID NO: 67, the 3'-Db-adapter is shown in SEQ ID NO: 68, and the 5'-Dbs-adapter is shown in SEQ ID NO: 69; (ii) the piR-2 is shown in SEQ ID NO: 56, the 3'-Db-adapter is shown in SEQ ID NO: 49, and the 5'-Dbs-adapter is shown in SEQ ID NO: 48; and (iii) the piR-2-[3'+ACCA] is shown in SEQ ID NO: 57, the 3'-Db-adapter is shown in SEQ ID NO: 30, and the 5'-Dbs-adapter is shown in SEQ ID NO: 48.

Dumbbell-PCR Quantification of Small RNAs in BmN4 Cells and Human Cancer Cell Lines To examine the feasibility and credibility of Db-PCR, piR-2 and piR-2-[3'+ACCA] were quantified in control and BmPAPI-depleted BmN4 cells (FIG. 14). As exactly shown by 3'-Db-PCR, upon BmPAPI depletion, Db-PCR quantification revealed a reduction in piR-2 levels, whereas the levels of piR-2-[3'+ACCA] were markedly upregulated (FIG. 5A). The Db-PCR recapitulation of the results from 3'-Db-PCR suggests the credibility and general versatility of both methods. Moreover, using Db-PCR, the expression profiles of miR-16 and miR-21 were determined in identical amounts of total RNA from eight different human cancer cell lines (FIG. 5B).

Each cell line exhibited a distinctive signature of the expression of the two miRNAs, and each miRNA showed a distinctive expression pattern in different cell lines. The high expression of miR-21 in MCF-7 compared with those in other breast cancer cell lines was consistent with a previous study of miRNA quantification by microarray analysis (50). Among prostate cancer cell lines, in a previous study, the most abundant miR-21 expression in DU145 cells was observed using Northern blot and Real-time PCR analyses (51), which is consistent with our Db-PCR results. These results indicate the credibility and potential broad applicability of Db-PCR.

FIG. 1. Provides a depiction of a schematic representation of 3'-Db-PCR (A), 5'-Db-PCR (B), and Db-PCR (C).

FIG. 2 provides a depiction of 3'-Db-PCR to quantify specific 3'-variants of small RNAs (FIG. 2A) Sequences and secondary structures of 3'-Db-adapter and targeted human miR-16. A, G, C, and T designate DNA, whereas rA, rG, rC, and rU designate RNA. The regions from which the primers and TaqMan® probe were derived are shown. An RT primer was used for reverse transcription, whereas forward (F) and reverse (R) primers and TaqMan® probe were used for Real-time PCR. (FIG. 2B) 3'-Db-PCR was applied for the detection of synthetic miR-16 and its 3'-variants, whose sequences are shown above. miR-16 but not its 3'-variants was specifically amplified by 3'-Db-PCR. The data represents the average Ct values from three independent experiments with bars showing the SD. Northern blot detection of the quantified RNAs is shown below. (FIG. 2C) Proportional correlation of HeLa total RNA input (0.313, 0.625, 1.25, 2.5 and 5 ng) to the Ct value obtained by 3'-Db-PCR. Each data set represents the average of three independent experiments with bars showing the SD. (FIG. 2D) 3'-Db-PCR was applied for the detection of *Bombyx* piR-1, piR-2, and their 3'-variants expressed in BmN4 cells treated with control or BmPAPI-targeting dsRNAs. The abundance in control cells was defined as 1 and the average relative abundance from three independent experiments are shown with SD bars.

Further depicted in FIG. 2 are SEQ ID NO: 5 for the F primer and SEQ ID NO: 18 for the R primer. In FIG. 2B SEQ ID NO: 5 for miR-15, SEQ ID NO: 7 for 3'+G and SEQ ID NO: 8 for 3'−G. Each being a variant of miR-16 adding or subtracting a G. FIG. 2D depicts SEQ ID NO: 54-SEQ ID NO: 57 corresponding to the top four RNA identified in FIG. 2D.

FIG. 3 depicts 5'-Db-PCR to quantify specific 5'-variants of small RNAs. (FIG. 3A) Depicts sequences and secondary structures of the 5'-Db-adapter and targeted human miR-16. The 5'-Db-adapter contains two 3'-terminal RNA nucleotides, whereas all other parts of the adapter consist of DNA. The regions from which primers and TaqMan® probe were derived are shown. FIG. 3B depicts 5'-Db-PCR was applied for the detection of synthetic miR-16 and its 5'-variants whose sequences are shown above. miR-16 but not its 5'-variants was specifically amplified by 5'-Db-PCR. The data represents the average Ct values from three independent experiments with bars showing the SD. Northern blot detection of the quantified RNAs is shown below. FIG. 3C depicts proportional correlation of HeLa total RNA input (0.313, 0.625, 1.25, 2.5, and 5 ng) to the Ct value obtained by 5'-Db-PCR. Each data set represents the average of three independent experiments with bars showing the SD. FIG. 3D depicts 5'-Db-PCR was applied for the detection of human miR-26a and miR-26a-[5'+A], a 5'-isomiR of miR-26a containing an additional A residue at its 5'-end, in HepG2, HEK293, and HeLa cell lines. The abundance in HepG2 cells was defined as 1, and the average of the relative abundance from three independent experiments are shown with SD bars. The average Ct values of miR-26a and miR-26a-[5'+A] from HepG2 cells were 26.55 and 30.10, respectively.

Figure 3D:
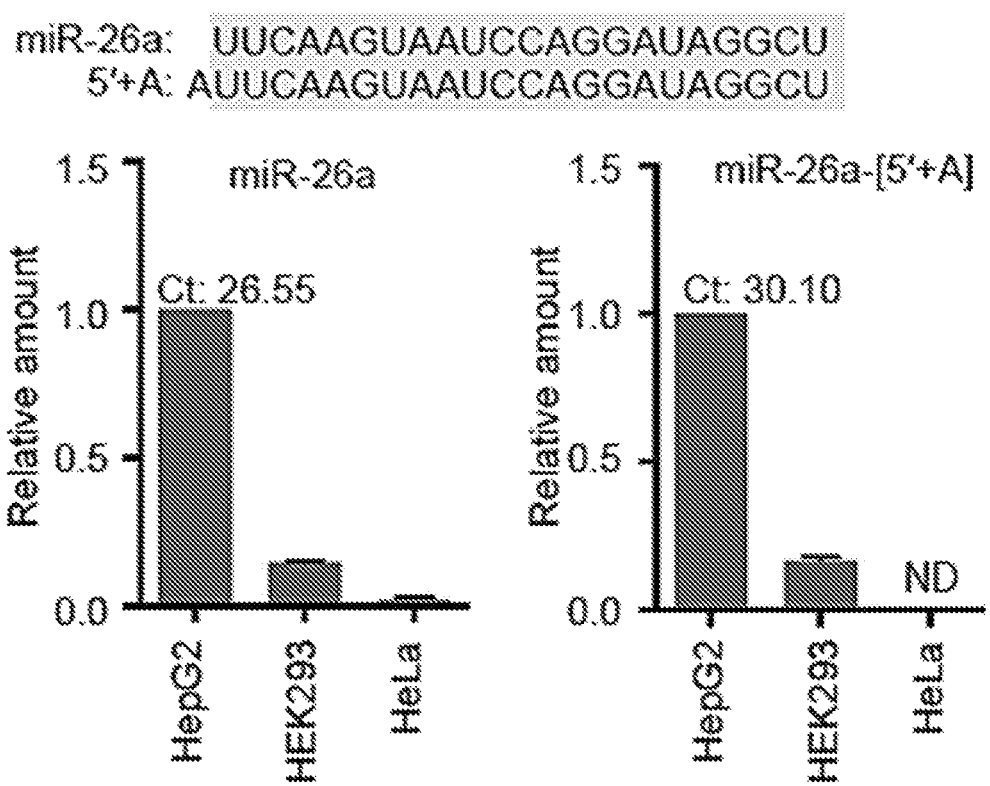
FIG. 3(D) demonstrates the capability of 3'-Db-PCR for discriminate quantification of small RNAs and their endogenous 3'-variants and (i) the miR-26a is shown in SEQ ID NO: 59 and (ii) the 5'+A is shown in SEQ ID NO: 60.

FIG. 3A depicts SEQ ID NO: 33 for the RT Primer and SEQ ID NO: 32, which corresponds to the 5' DB-adapter. FIG. 3B depicts SEQ ID NO: 5 for the miR-16 and variants adding or subtracting a U, for SEQ ID NO: 6 and SEQ ID NO: 58. FIG. 3D depicts SEQ ID NO: 59 for the miR-26A and SEQ ID NO: 60 for the 5' variant.

FIG. 4. Db-PCR to specifically quantify miR-16. In FIG. 4A, sequences and secondary structures of the 5'-Dbs-adapter, 3'-Db-adapter, and targeted human miR-16 are depicted. The 5'-Dbs-adapter contains two 3'-terminal RNA nucleotides and a spacer in the loop region. Three different 5'-Dbs-adapters containing 6, 12, or 16 nucleotides protruding from the 5'-end were used. The regions from which primers and TaqMan® probe were derived are also shown. FIG. 4A depicts primers from table S1 and table S3. FIG. 4C depicts miR-16 and variants of U, G, and G from the 3' and 5' ends corresponding to SEQ ID NO: 5, 6, 7, 8, 9, 10, and 61, as described below in greater detail. FIG. 4D depicts SEQ ID NO: 5, 6, and 10.

FIG. 4B depicts Db-PCR using a 5'-Dbs-adapter with 6, 12, or 16 nucleotides protruding from the 5'-end was applied for the detection of synthetic miR-16. The 5'-Dbs-adapter with 16-nt protruding end showed the highest detection efficiency. The data represents the average Ct value from three independent experiments with bars showing the SD. FIGS. 4C, 4D depict Db-PCR was applied for the detection of synthetic miR-16 and its 5'- and 3'-variants whose sequences are shown above the graph. miR-16 was the only RNA species amplified by the Db-PCR. The data represents the average Ct value from three independent experiments with bars showing the SD. Northern blot detection of the quantified RNAs is shown below. FIG. 4E identifies proportional correlation of HeLa total RNA input (0.313, 0.625, 1.25, 2.5, and 5 ng) to the Ct value obtained by Db-PCR. Each data set represents the average of three independent experiments with bars showing the SD.

FIG. 5 shows small RNA quantifications by Db-PCR in BmN4 and human cancer cell lines. In FIG. 5A, piRNAs and their variants in control or BmPAPI-depleted BmN4 cells were quantified by Db-PCR. The abundance in control cells was defined as 1, and the average of relative piRNA amounts from three independent experiments are shown with SD bars. FIG. 5B shows comparison of the abundance of the miR-16 and miR-21, determined by Db-PCR, in human breast cancer cell lines (MCF-7, SK-BR-3, BT-474, and MDA-MB-231), prostate cancer cell lines (DU145, PC-3 and LNCaP-FGC), and HeLa cells. The abundance in HeLa cells was defined as 1. Each data set represents the average relative abundance from three independent experiments with bars showing the SD.

FIG. 6 shows standard RT-PCR using stem-loop primer is not capable of distinguishing 3'-variants of miRNA. In FIG. 6A, schematic representation of a standard RT-PCR using a stem-loop RT primer for miRNA quantification (37). A stem-loop RT primer was specifically hybridized to the 3'-end of the target RNA, followed by reverse transcription. The resultant cDNA was amplified and quantified by Real-time PCR using forward and reverse primers derived from the targeted miRNA and RT primer, respectively. (FIG. 6B—also depicting SEQ ID NO: 5, 7, and 8). The standard RT-PCR was designed to target miR-16, which was applied for the detection of synthetic miR-16 and its 3'-variants whose sequences are shown above the graph. The method was performed as previously reported (37) with minor modifications. For reverse transcription, synthetic miR-16 or its 3'-variants (200 amol) was incubated in the reaction mixture (20 µL volume) containing SuperScript® III Reverse Transcriptase (Life Technologies) and 1 pmol of stem-loop RT primer (5'-GTCGTATCCAGT GCAGGG-TCCGAGGTATTCGCACTGGATACGACCGCCAA-3') (SEQ ID NO: 4) at 16° C. for 30 min, followed by incubation at 42° C. for 30 min. The resultant cDNA solution was diluted to 1:5, and 1.5 µL of this solution was used for the Real-time PCR reaction (10 µL volume) using SsoFast EvaGreen® Supermix (BioRad) and StepOne Plus Real-time PCR machine (Applied Biosystems). The miR-16 and its 3'-variants were similarly detected by the method, indicating that the method does not have a resolution to distinguish target RNA from its 3'-variants.

FIG. 7. depicts a schematic representation of the quantification of miR-16 by 3'-Db-PCR. Depicted are sequences for miR-16 (SEQ ID NO: 5) and various adapters including 3'-DB-adapter SEQ ID NO: 18, and two primers SEQ ID NO: 12 and 13. Also shown is a forward primer SEQ ID NO: 20 and the TaqMan® Probe corresponding to sequences in Tables S1-S3.

FIG. 8 depicts 5'-Db-PCR, 3'-Db-PCR, and Db-PCR amplified cDNAs as a clear band wherein the amplified cDNAs resulting from 5'-Db-PCR (5'-Db), 3'-Db-PCR (3'-Db), and Db-PCR (Db) for detection of miR-16 and miR-21 in HeLa total RNA were developed by 3% Metaphor gel electrophoresis (LONZA). The expected band sizes from the 5'-Db-PCR, 3'-Db-PCR, and Db-PCR are 59, 49, and 66 bp, respectively; a clear band with the expected size was observed in all lanes.

FIG. 9 depicts proportional correlation of miR-16 input to the Ct value obtained by 3'-Db-PCR, 5'-Db-PCR, and Db-PCR Synthetic miR-16 (0.0156, 0.0625, 0.125, 0.25, and 1 fmol) were quantified by 3'-Db-PCR, 5'-Db-PCR, and Db-PCR. Each data set represents the average of three independent experiments with bars showing the SD.

Figure 10:
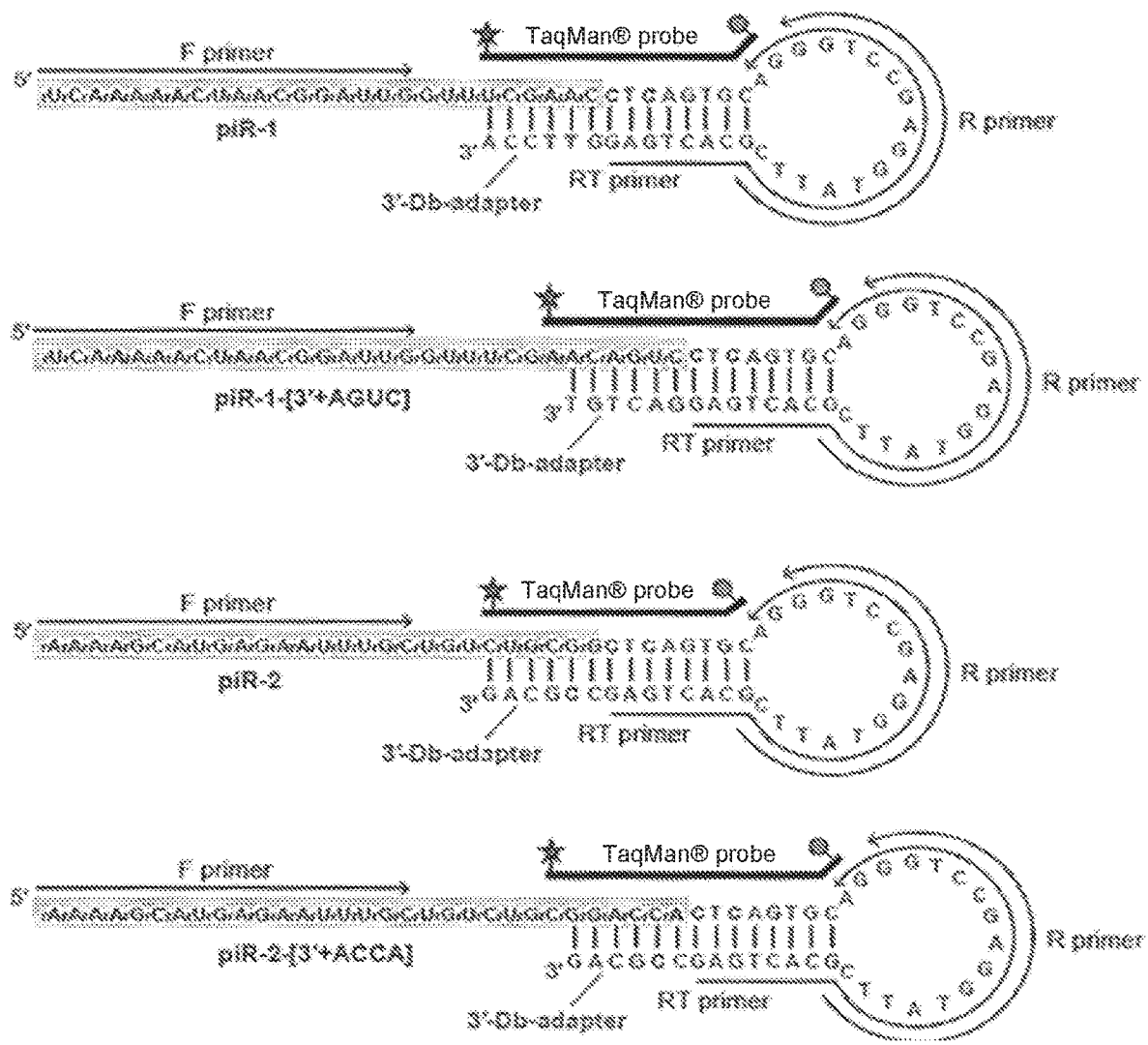
FIG. 10 depicts sequences and secondary structures of the 3'-Db-adapter and targeted Bombyx piRNAs quantified by 3'-Db-PCR and the piR RNAs, which are contained in the grey boxes from top to bottom, are (i) SEQ ID NO: 64, (ii) SEQ ID NO: 65, (iii) SEQ ID NO: 56, and (iv) SEQ ID NO: 57, which correspond with 3'-Db-adapter sequences SEQ ID NO: 63, SEQ ID NO: 25, SEQ ID NO: 49; and SEQ ID NO: 49, respectively. The regions of the piR target and the 3'-Db-adapter targeted by the F primer, the RT primer, the R primer, and the probe are shown in FIG. 10.

FIG. 10 depicts sequences and secondary structures of the 3'-Db-adapter and targeted *Bombyx* piRNAs quantified by 3'-Db-PCR. Depicted the piR RNAs, which are contained in the grey boxes from top to bottom, corresponding to SEQ ID NO: 64, SEQ ID NO: 65, SEQ ID NO: 56, and SEQ ID NO: 57. Corresponding RT Primers for the piR-1 and piR-2 and variants are also depicted in Tables S1 and S3.

FIG. 11 depicts a schematic representation of the quantification of miR-16 by 5'-Db-PCR. The appropriate sequences for FIG. 11 are depicted in complete in Tables S1-S3.

FIG. 12 depicts sequences and secondary structures of the 5'-Db-adapter, shown in SEQ ID NO: 66, and targeted human microRNAs quantified by 5'-Db-PCR. The miR RNAs are shown, from top to bottom, in (i) SEQ ID NO: 59; and (ii) SEQ ID NO: 60.

FIG. 13 depicts schematic representation of the quantification of miR-16 by Db-PCR. Corresponding primers and adapters are depicted in tables S1-S3.

FIG. 14 depicts sequences and secondary structures of the adapters and targeted small RNAs quantified by Db-PCR. Various probes from top to bottom are (i) the miR-21 is shown in SEQ ID NO: 67; (ii) the piR-2 is shown in SEQ ID NO: 56; and (iii) the piR-2-[3'+ACCA] is shown in SEQ ID NO: 57, and the remaining sequences are depicted in tables S1-S3.

Materials and Methods

Cell culture, RNAi knockdown, and total RNA isolation

HeLa, HEK293, and BT-474 cells were cultured in Dulbecco's modified Eagle's medium (DMEM; Life Technologies) containing 10% fetal bovine serum (FBS). SK-BR-3, DU145, PC-3, and LNCaP-FGC cell lines were cultured in RMPI1640 medium (Life Technologies) containing 10% FBS. The HepG2 cell line was cultured in minimum essential medium (MEM; Life Technologies) containing 10% FBS. The MDA-MB-231 cell line was cultured in L-15 medium (Life Technologies) containing 10% FBS, and the MCF-7 cell line was cultured in MEM medium containing 10% FBS, 1 mM sodium pyruvate, 1× non-essential amino acids solution (Life Technologies), and 10 µg/ml insulin (Sigma). Culture of the *Bombyx mori* BmN4 cell line and RNAi knockdown of BmPAPI were performed as previously described (45).

Briefly, BmN4 cells were cultured at 27° C. in Insect-Xpress medium (LONZA). For RNAi knockdown of BmPAPI, in vitro synthesized BmPAPI-targeting dsRNA or control Renilla luciferase-targeting dsRNA (5 µg) was transfected into 5×106 BmN4 cells using the 4D-Nucleofector System (LONZA), and cells were harvested 4 days after transfection. Total RNA from all cell lines was extracted using TRIsure® reagent (Bioline) according to the manufacturer's protocol.

Synthetic miRNA and its Variants

To examine detection specificities of Db-PCR, the synthetic human miR-16 (5'-P-UAGCAGCACGUAAAUAUUGGCG-3') (SEQ ID NO: 5), its 5'-variants (5'+1: 5'-P-UUAGCAGCACGU-AAAUAUUGGCG-3' (SEQ ID NO: 6); 5'−1: 5'-P-AGCAGCACGUAAAUAUUGGCG-3') (SEQ ID NO: 61), its 3'-variants (3'+1: 5'-P-UAGCAGCACGU-AAAUAUUGGCGG-3' (SEQ ID NO: 7); 3'−1: 5'-P-UAGCAGCACGUAAAUAUUGGC-3') (SEQ ID NO: 8), and its 5'- and 3'-variants (5'+1/3'−1: 5'-P-UUAGCAGCACGUAAAUAUUGGC-3' (SEQ ID NO: 9); 5'−1/3'+1: 5'-P-AGCAGCACGUAAAUAUUGGCGG-3') (SEQ ID NO: 10) were synthesized by Integrated DNA Technologies. Integrated DNA Technologies also synthesized all the adapters and primers used in this study described below. Northern blot analyses against these synthetic RNAs were performed as described previously (45) by using a 5'-end labeled antisense probe (5'GCCAATATT-TACGTGCTGCTA-3') (SEQ ID NO: 11).

3'-Db-PCR to Quantify a Specific 3'-Variant of Small RNAs

The sequences of adapters and primers used for 3'-Db-PCR are shown in Supplementary Table S1. To detect miR-16 by 3'-Db-PCR, a DNA 3'-Db-adapter (SEQ ID NO: 1) was designed by using mfold program (46) to form a stem-loop structure with 6 nucleotides protruding from the 3'-end that hybridizes with the 3'-terminal sequences of miR-16. The loop sequences of the 3'-Db-adapter were identical with those of a stem-loop primer for miRNA quantification (37). Synthetic miR-16, its variants (20 fmol each), or 1 µg of cellular total RNA was incubated with 20 pmol of the 3'-Db-adapter in a 9-µL reaction mixture at 90° C. for 3 min. After adding 1 µL of 10× annealing buffer containing 50 mM Tris-HC1 (pH 8.0), 5 mM EDTA, and 100 mM MgC12, the total 10-µL mixture was annealed by incubation at 37° C. for 20 min. To ligate the annealed adapter to miR-16, 10 µL of the 1× reaction buffer containing 1 U of Rnl2 (New England Biolabs) was added to the mixture. The entire mixture (20 µL) was incubated at 37° C. for 1 h, followed by overnight incubation at 4° C. For reverse transcription, the ligated RNA (1 µL) was mixed with dNTP and RT primer (5'-CTCAGTGCGAAT-ACCTCGGACCCT-3', SEQ ID NO: 12), and the 7-µL mixture was incubated at 90° C. for 2 min, followed by incubation on ice. The mixture was then subjected to reverse transcription reaction (10 µL volume) using SuperScript® III Reverse Transcriptase (Life Technologies) at 55° C. for 60 min. The resultant cDNA solution was diluted to 1:5 and 1.5 µL of this solution was added to the Real-time PCR mixture containing 5 µL of 2>< Premix Ex Taq reaction solution (Clontech Laboratories), 100 nM TaqMan® probe, and 2 pmol each of the forward primer complementary to targeted RNA and a reverse primer (5'-CGAATACCTC-GGACC-3', SEQ ID NO: 13) (10 µL in total). With the StepOne Plus Real-time PCR system (Applied Biosystems), the reaction mixture was incubated at 95° C. for 20 s, followed by 30 or 40 cycles of 95° C. for 1 s and 60° C. for 20 s. For detection of *Bombyx* piRNA-1 (piR-1), piRNA-2 (piR-2), and their corresponding 3'-variants, piR-1-[3'+AGUC] and piR-2-[3'+ACCA], present in BmN4 cells (45), Real-time PCR was performed with 400 nM of TaqMan® probe, and the reaction mixture was incubated at 95° C. for 20 s, followed by 40 cycles of 95° C. for 1 s and 50° C. or 60° C. for 20 s for piR-1 or piR-2, respectively.

Table S1 provides the following sequences in order:

SEQ ID NO: 18, SEQ ID NO: 19, SEQ ID NO: 13, SEQ ID NO: 20, SEQ ID NO: 21 for miR-16.

SEQ ID NO: 22, SEQ ID NO: 19, SEQ ID NO: 13, SEQ ID NO: 23, SEQ ID NO: 24 for piR-1.

SEQ ID NO: 25, SEQ ID NO: 19, SEQ ID NO: 13, SEQ ID NO: 23, SEQ ID NO: 26 for piR-1-[3'+AGUC].

SEQ ID NO: 27, SEQ ID NO: 19, SEQ ID NO:13, SEQ ID NO: 28, SEQ ID NO: 29 for piR-2.

SEQ ID NO: 30, SEQ ID NO: 19, SEQ ID NO: 13, SEQ ID NO: 28, SEQ ID NO: 31 for piR-2-[3'+ACCA].

5'-Db-PCR to Quantify a Specific 5'-Variant of Small RNAs

The sequences of adapters and primers used for 5'-Db-PCR are shown in Supplementary Table S2. To detect miR-16 by 5'-Db-PCR, a DNA/RNA hybrid 5'-Db-adapter (SEQ ID NO: 2) was designed to form a stem-loop structure with 6 nucleotides protruding from the 5'-end to hybridize the 5'-terminal sequences of miR-16. The ligation of the 5'-Db-adapter to miR-16 or its variants and Real-time RT-PCR were performed in the same procedure of 3'-Db-PCR for miR-16 as described above. For detection of miR-26a and its 5'-variant, miR-26a-[5'±A], Real-time PCR was performed with 400 nM of TaqMan® probe and 2 pmol each of a forward primer (5'-GAGGGTGTGTGGTCTT-3', SEQ ID NO: 14) and a reverse primer complementary to targeted RNA by incubating the reaction mixture at 95° C. for 20 s, followed by 40 cycles of 9.5° C. for 1 s and 5.5° C. for 20 s.

Table S2 provides the following sequences:

SEQ ID NO: 32, SEQ ID NO: 33, SEQ ID NO: 33, SEQ ID NO: 14, SEQ ID NO: 34 for miR-16.

SEQ ID NO: 35, SEQ ID NO: 36, SEQ ID NO: 36, SEQ ID NO: 14, SEQ ID NO: 37 for miR-26a.

SEQ ID NO: 38, SEQ ID NO: 36, SEQ ID NO: 36, SEQ ID NO: 14, SEQ ID NO: 62 for miR-26a-[5'+A].

Db-PCR to Quantify Small RNA Variants with Distinct 5'- and 3'-Terminal Sequences The sequences of adapters and primers used for Db-PCR are shown in Supplementary Table S3. To detect small RNAs by Db-PCR, a DNA/RNA hybrid 5'-Dbs-adapter (SEQ ID NO: 3) was designed to form a stem-loop structure containing a base-lacking 1', 2'-dideoxyribose spacer in the loop region and a protruding 5'-end complementary to the 5'-terminal sequences of target RNAs. The 5'-Dbs-adapter (20 pmol) was hybridized to 20 fmol of synthetic small RNA, its variants, or 1 µg of cellular total RNA in a 10-µL mixture using the same procedure with 5'-Db-PCR as described above. After adding 10 µL of the 1× reaction buffer containing 1 U of Rnl2 (New England Biolabs), the entire mixture (20 µL) was incubated at 37° C. for 30 min. Subsequently, 20 pmol 3'-Db-adapter (1 µL, SEQ ID NO: 1) was added to the reaction mixture, followed by a 30-min incubation at 16° C. and then overnight incubation at 4° C. Real-time RT-PCR was performed using the same procedure as described for 3'-Db-PCR with 400 nM TaqMan® probe concentration and using a reverse primer (SEQ ID NO: 5) and a forward primer (5'-TGGAGTGTGTGCT-TTGACGXXXX-3' (SEQ ID NO: 15) whose 3'-terminal 4 nucleotides XXXX designate the sequences corresponding to 5'-terminal sequences of a target RNA; SEQ ID NO: 7). These reaction mixtures were incubated at 95° C. for 20 s, followed by 40 cycles of 95° C. for 1 s and 62° C. for 20 s. U6 snRNA expression was quantified for use as an internal control using SsoFast EvaGreen® Supermix (BioRad) and the following primers: forward, 5'-TCGCTTCGGCAGCA-CATATAC-3' (SEQ ID NO: 16) and reverse, 5'-CGAAT-TTGCGTGTCATCCTTG-3' (SEQ ID NO: 17).

Table S3 provides a list of the following Sequences in order from top to bottom:

SEQ ID NO: 39, SEQ ID NO: 40, SEQ ID NO: 41, SEQ ID NO: 42, SEQ ID NO: 12, SEQ ID NO: 13, SEQ ID NO: 43, SEQ ID NO: 44 for miR-16.

SEQ ID NO: 45, SEQ ID NO: 46, SEQ ID NO: 12, SEQ ID NO: 13, SEQ ID NO: 43, SEQ ID NO: 47 for miR-21.

SEQ ID NO: 48, SEQ ID NO: 49, SEQ ID NO: 12, SEQ ID NO: 13, SEQ ID NO: 50, SEQ ID NO: 51 for piR-2.

SEQ ID NO: 52, SEQ ID NO: 53, SEQ ID NO: 12, SEQ ID NO: 13, SEQ ID NO: 50, SEQ ID NO: 31 for piR-2-[3'+ACCA].

Conclusions

Accordingly, the embodiments herein describe several new methods that are efficient and convenient methods to selectively quantify variants of small RNAs by utilizing stem-loop adapter ligations followed by TaqMan® RT-PCR. The 5'- and 3'-Db-PCR methods are useful to distinctively quantify 5'- and 3'-variants of small RNAs, respectively. Db-PCR simultaneously identifies specific 5'- and 3'-terminal sequences of target RNAs and quantifies a single small RNA species with specific terminal sequences. These methods provide a much-needed simple method to analyze terminal sequence variations of small RNAs, as these factors may play important roles in various biological processes. These methods can also shed light on the biological significance of small RNAs coexisting with abundant precursor RNAs in the cells, such as functional tRNA fragments (52), for which specific detection and quantification require discrimination.

REFERENCES

1. Esteller, M. (2011) Non-coding RNAs in human disease. Nat Rev Genet, 12, 861874.
2. Bartel, D. P. (2009) MicroRNAs: target recognition and regulatory functions. Cell, 136, 215-233.
3. Siomi, M. C., Sato, K., Pezic, D. and Aravin, A. A. (2011) PIWI-interacting small RNAs: the vanguard of genome defence. Nat Rev Mol Cell Biol, 12, 246-258.
4. Okamura, K. and Lai, E. C. (2008) Endogenous small interfering RNAs in animals. Nat Rev Mol Cell Biol, 9, 673-678.
5. Ghildiyal, M. and Zamore, P. D. (2009) Small silencing RNAs: an expanding universe. Nat Rev Genet, 10, 94-108.
6. Farazi, T. A., Juranek, S. A. and Tuschl, T. (2008) The growing catalog of small RNAs and their association with distinct Argonaute/Piwi family members. Development, 135, 1201-1214.
7. Liu, X., Fortin, K. and Mourelatos, Z. (2008) MicroRNAs: biogenesis and molecular functions. Brain Pathol, 18, 113-121.
8. Pillai, R. S., Bhattacharyya, S. N. and Filipowicz, W. (2007) Repression of protein synthesis by miRNAs: how many mechanisms? Trends Cell Biol, 17, 118-126.
9. Kozomara, A. and Griffiths-Jones, S. (2014) miRBase: annotating high confidence microRNAs using deep sequencing data. Nucleic Acids Res, 42, D68-73.
10. Friedman, R. C., Farh, K. K., Burge, C. B. and Bartel, D. P. (2009) Most mammalian mRNAs are conserved targets of microRNAs. Genome Res, 19, 92-105.
11. Neilsen, C. T., Goodall, G. J. and Bracken, C. P. (2012) IsomiRs—the overlooked repertoire in the dynamic microRNAome. Trends in genetics: TIG, 28, 544-549.
12. Morin, R. D., O'Connor, M. D., Griffith, M., Kuchenbauer, F., Delaney, A., Prabhu, A. L., Zhao, Y., McDonald, H., Zeng, T., Hirst, M. et al. (2008) Application of massively parallel sequencing to microRNA profiling and discovery in human embryonic stem cells. Genome Res, 18, 610-621.
13. Newman, M. A., Mani, V. and Hammond, S. M. (2011) Deep sequencing of microRNA precursors reveals extensive 3' end modification. Rna, 17, 1795-1803.
14. Starega-Roslan, J., Krol, J., Koscianska, E., Kozlowski, P., Szlachcic, W. J., Sobczak, K. and Krzyzosiak, W. J. (2011) Structural basis of microRNA length variety. Nucleic acids research, 39, 257-268.
15. Liu, N., Abe, M., Sabin, L. R., Hendriks, G. J., Naqvi, A. S., Yu, Z., Cherry, S. and Bonini, N. M. (2011) The exoribonuclease Nibbler controls 3' end processing of microRNAs in Drosophila. Current biology: CB, 21, 1888-1893.
16. Han, B. W., Hung, J. H., Weng, Z., Zamore, P. D. and Ameres, S. L. (2011) The 3'-to-5' exoribonuclease Nibbler shapes the 3' ends of microRNAs bound to Drosophila Argonautel. Current biology: CB, 21, 1878-1887.
17. Landgraf, P., Rusu, M., Sheridan, R., Sewer, A., Iovino, N., Aravin, A., Pfeffer, S., Rice, A., Kamphorst, A. O., Landthaler, M. et al. (2007) A mammalian microRNA expression atlas based on small RNA library sequencing. Cell, 129, 1401-1414.
18. Blow, M. J., Grocock, R. J., van Dongen, S., Enright, A. J., Dicks, E., Futreal, P. A., Wooster, R. and Stratton, M. R. (2006) RNA editing of human microRNAs. Genome biology, 7, R27.
19. Kawahara, Y., Zinshteyn, B., Sethupathy, P., Iizasa, H Hatzigeorgiou, A. G. and Nishikura, K. (2007) Redirection of silencing targets by adenosine-to-inosine editing of miRNAs. Science, 315, 1137-1140.
20. Burroughs, A. M., Ando, Y., de Hoon, M. J., Tomaru, Y., Suzuki, H., Hayashizaki, Y. and Daub, C. O. (2011) Deep-sequencing of human Argonaute-associated small RNAs provides insight into miRNA sorting and reveals Argonaute association with RNA fragments of diverse origin. RNA Biol, 8, 158-177.

21. Azuma-Mukai, A., Oguri, H., Mituyama, T., Qian, Z. R., Asai, K., Siomi, H. and Siomi, M. C. (2008) Characterization of endogenous human Argonautes and their miRNA partners in RNA silencing. Proceedings of the National Academy of Sciences of the United States of America, 105, 7964-7969.

22. Cloonan, N., Wani, S., Xu, Q., Gu, J., Lea, K., Heater, S., Barbacioru, C., Steptoe, A. L., Martin, H. C., Nourbakhsh, E. et al. (2011) MicroRNAs and their isomiRs function cooperatively to target common biological pathways. Genome biology, 12, R126.

23. Loher, P., Londin, E. R. and Rigoutsos, I. (2014) IsomiR Expression Profiles in Human Lymphoblastoid Cell Lines Exhibit Population and Gender Dependencies. Oncotarget, 5, 8790-8802.

24. Takeda, A., Iwasaki, S., Watanabe, T., Utsumi, M. and Watanabe, Y. (2008) The mechanism selecting the guide strand from small RNA duplexes is different among argonaute proteins. Plant & cell physiology, 49, 493-500.

25. Montgomery, T. A., Howell, M. D., Cuperus, J. T., Li, D., Hansen, J. E., Alexander, A. L., Chapman, E. J., Fahlgren, N., Allen, E. and Carrington, J. C. (2008) Specificity of ARGONAUTE7-miR390 interaction and dual functionality in TA8 trans-acting siRNA formation. Cell, 133, 128-141.

26. Mi, S., Cai, T., Hu, Y., Chen, Y., Hodges, E., Ni, F., Wu, L., Li, S., Zhou, H., Long, C. et al. (2008) Sorting of small RNAs into Arabidopsis argonaute complexes is directed by the 5' terminal nucleotide. Cell, 133, 116-127.

27. Czech, B., Zhou, R., Erlich, Y., Brennecke, J., Binari, R., Villalta, C., Gordon, A., Perrimon, N. and Hannon, G. J. (2009) Hierarchical rules for Argonaute loading in Drosophila. Molecular cell, 36, 445-456.

28. Meijer, H. A., Smith, E. M. and Bushell, M. (2014) Regulation of miRNA strand selection: follow the leader? Biochemical Society transactions, 42, 1135-1140.

29. Lu, S., Sun, Y. H. and Chiang, V. L. (2009) Adenylation of plant miRNAs. Nucleic acids research, 37, 1878-1885.

30. Katoh, T., Sakaguchi, Y., Miyauchi, K., Suzuki, T., Kashiwabara, S., Baba, T. and Suzuki, T. (2009) Selective stabilization of mammalian microRNAs by 3' adenylation mediated by the cytoplasmic poly(A) polymerase GLD-2. Genes & development, 23, 433-438.

31. Boele, J., Persson, H., Shin, J. W., Ishizu, Y., Newie, I. S., Sokilde, R., Hawkins, S. M., Coarfa, C., Ikeda, K., Takayama, K. et al. (2014) PAPD5-mediated 3' adenylation and subsequent degradation of miR-21 is disrupted in proliferative disease. Proceedings of the National Academy of Sciences of the United States of America, 111, 11467-11472.

32. Tan, G. C., Chan, E., Molnar, A., Sarkar, R., Alexieva, D., Isa, I. M., Robinson, S., Zhang, S., Ellis, P., Langford, C. F. et al. (2014) 5' isomiR variation is of functional and evolutionary importance. Nucleic acids research, 42, 9424-9435.

33. Kozubek, J., Ma, Z., Fleming, E., Duggan, T., Wu, R., Shin, D. G. and Dadras, S. S. (2005) In-depth characterization of microRNA transcriptome in melanoma. PloS one, 8, e72699.

34. mel, M., Guo, S., Fu, N., Yan, Z., Hu, H. Y., Xu, Y., Yuan, Y., Ning, Z., Hu, Y Menzel, C. et al. (2010) MicroRNA, mRNA, and protein expression link development and aging in human and macaque brain. Genome research, 20, 1207-1218.

35. Fernandez-Valverde, S. L., Taft, R. J. and Mattick, J. S. (2010) Dynamic isomiR regulation in Drosophila development. Rna, 16, 1881-1888.

36. Bizuayehu, T. T., Lanes, C. F., Furmanek, T., Karlsen, B. O., Fernandes, J. M., Johansen, S. D. and Babiak, I. (2012) Differential expression patterns of conserved miRNAs and isomiRs during Atlantic halibut development. BMC genomics, 13, 11.

37. Chen, C., Ridzon, D. A., Broomer, A. J., Zhou, Z., Lee, D. H., Nguyen, J. T., Barbisin, M., Xu, N. L., Mahuvakar, V. R., Andersen, M. R. et al. (2005) Real-time quantification of microRNAs by stem-loop RT-PCR. Nucleic Acids Res, 33, e179.

38. Schamberger, A. and Orban, T. I. (2014) 3' IsomiR species and DNA contamination influence reliable quantification of microRNAs by stem-loop quantitative PCR. PLoS One, 9, e106315.

39. Ho, C. K. and Shuman, S. (2002) Bacteriophage T4 RNA ligase 2 (gp24.1) exemplifies a family of RNA ligases found in all phylogenetic domains. Proceedings of the National Academy of Sciences of the United States of America, 99, 12709-12714.

40. Bullard, D. R. and Bowater, R. P. (2006) Direct comparison of nick-joining activity of the nucleic acid ligases from bacteriophage T4. Biochem J, 398, 135-144.

41. Nandakumar, J., Ho, C. K., Lima, C. D. and Shuman, S. (2004) RNA substrate specificity and structure-guided mutational analysis of bacteriophage T4 RNA ligase 2. J Biol Chem, 279, 31337-31347.

42. Nandakumar, J. and Shuman, S. (2005) Dual mechanisms whereby a broken RNA end assists the catalysis of its repair by T4 RNA ligase 2. J Biol Chem, 280, 23484-23489.

43. Clepet, C. (2011) RNA captor: a tool for RNA characterization. PloS one, 6, e18445.

44. Park, K., Choi, B. R., Kim, Y. S., Shin, S., Hah, S. S., Jung, W., Oh, S. and Kim, D. E. (2011) Detection of single-base mutation in RNA using T4 RNA ligase-based nick-joining or DNAzyme-based nick-generation. Analytical biochemistry, 414, 303-305.

45. Honda, S., Kirino, Y., Maragkakis, M., Alexiou, P., Ohtaki, A., Murali, R. and Mourelatos, Z. (2013) Mitochondrial protein BmPAPI modulates the length of mature piRNAs. RNA, 191405-1418.

46. Zuker, M. (2003) Mfold web server for nucleic acid folding and hybridization prediction. Nucleic Acids Res, 31, 3406-3415.

47. Ranade, K., Chang, M. S., Ting, C. T., Pei, D., Hsiao, C. F., Olivier, M., Pesich, R., Hebert, J., Chen, Y. D., Dzau, V. J. et al. (2001) High-throughput genotyping with single nucleotide polymorphisms. Genome research, 11, 1262-1268.

48. Lagos-Quintana, M., Rauhut, R., Meyer, J., Borkhardt, A. and Tuschl, T. (2003) New microRNAs from mouse and human. Rna, 9, 175-179.

49. Kawaoka, S., Hayashi, N., Suzuki, Y., Abe, H., Sugano, S., Tomari, Y., Shimada, T. and Katsuma, S. (2009) The Bombyx ovary-derived cell line endogenously expresses PIWI/PIWI-interacting RNA complexes. RNA, 15, 1258-1264.

50. Riaz, M., van Jaarsveld, M. T., Hollestelle, A., Prager-van der Smissen, W. J., Heine, A. A., Boersma, A. W., Liu, J., Helmijr, J., Ozturk, B., Smid, M. et al. (2013) miRNA expression profiling of 51 human breast cancer cell lines reveals subtype and driver mutation-specific miRNAs. Breast cancer research: BCR, 15, R33.

51. Li, T., Li, D., Sha, J., Sun, P. and Huang, Y. (2009) MicroRNA-21 directly targets MARCKS and promotes apoptosis resistance and invasion in prostate cancer cells. Biochemical and biophysical research communications, 383, 280-285.

52. Shigematsu, M., Honda, S. and Kirino, Y. (2014) Transfer RNA as a Source of Small Functional RNA. Journal of Molecular Biology and Molecular Imaging, 1, 8.

SUPPLEMENTARY TABLE S1

Sequenes of adaptors and primers for 3'-Db-PCR

| Target | Primer/adapter | Sequence (5'-3') |
|---|---|---|
| miR-16 | 3'-Db-adapter | /5Phos/CTCAGTGCAGGGTCCGAGGTATTCGCACTGAGCGCCAA (SEQ ID NO: 18) |
| | RT primer | CTCAGTGCGAATACCTCGGACCCT (SEQ ID NO: 19) |
| | Reverse primer | CGAATACCTCGGACC (SEQ ID NO: 13) |
| | Forward primer | GCGCTAGCAGCACGTAAATAT (SEQ ID NO: 20) |
| | TaqMan® probe | /56-FAM/TGGCGCTCA/ZEN/GTG/3IABkFQ/ (SEQ ID NO: 21) |
| piR-1 | 3'-Db-adapter | /5phos/CTCAGTGCAGGGTCCGAGGTATTCGCACTGAGGTTCGA (SEQ ID NO: 22) |
| | RT primer | CTCAGTGCGAATACCTCGGACCCT (SEQ ID NO: 19) |
| | Reverse primer | CGAATACCTCGGACC (SEQ ID NO: 13) |
| | Forward primer | TCAAAAACTAACGGATTG (SEQ ID NO: 23) |
| | TaqMan® probe | /56-FAM/TCGAACCTC/ZEN/AGTGCAG/3IABkFQ/ (SEQ ID NO: 24) |
| piR-1-[3' + AGUC] | 3'-Db-adapter | /5Phos/CTCAGTGCAGGGTCCGAGGTATTCGCACTGAGGACTGT (SEQ ID NO: 25) |
| | RT primer | CTCAGTGCGAATACCTCGGACCCT (SEQ ID NO: 19) |
| | Reverse primer | CGAATACCTCGGACC (SEQ ID NO: 13) |
| | Forward primer | TCAAAAACTAACGGATTG (SEQ ID NO: 23) |
| | TaqMan® probe | /56-FAM/AACAGTCCT/ZEN/CAGTGCAG/3IABkFQ/ (SEQ ID NO: 26) |
| piR-2 | 3'-Db-adapter | /5Phos/CTCAGTGCAGGGTCCGAGGTATTCGCACTGAGCCGCAG (SEQ ID NO: 27) |
| | RT primer | CTCAGTGCGAATACCTCGGACCCT (SEQ ID NO: 19) |
| | Reverse primer | CGAATACCTCGGACC (SEQ ID NO: 13) |
| | Forward primer | AAAAGCATGAGAATTTGC (SEQ ID NO: 28) |
| | TaqMan® probe | /56-FAM/CTGCGGCTC/ZEN/AGTGCA/3IABkFQ/ (SEQ ID NO: 29) |
| piR-2-[3' + ACCA] | 3'-Db-adapter | /5Phos/CTCAGTGCAGGGTCCGAGGTATTCGCACTGAGTGGTCC (SEQ ID NO: 30) |
| | RT primer | CTCAGTGCGAATACCTCGGACCCT (SEQ ID NO: 19) |
| | Reverse primer | CGAATACCTCGGACC (SEQ ID NO: 13) |
| | Forward primer | AAAAGCATGAGAATTTGC (SEQ ID NO: 28) |
| | TaqMan® probe | /56-FAM/CGGACCACT/ZEN/CAGTGCAG/3IABkFQ/ (SEQ ID NO: 31) |

SUPPLEMENTARY TABLE S2

Sequences of adapters and primers for 5'-Db-PCR

| Target | Primer/adapter | Sequence (5'-3') |
|---|---|---|
| miR-16 | 5'-Db-adapter | CTGCTACTCAGTGCGTGGGAGGGTGTGTGGTCTTGCTTGGTGTGCACTGrArG (SEQ ID NO: 32) |
| | RT primer | GCGACGCCAATATTTACGTG (SEQ ID NO: 33) |
| | Reverse primer | GCGACGCCAATATTTACGTG (SEQ ID NO: 33) |
| | Forward primer | GAGGGTGTGTGGTCTT (SEQ ID NO: 14) |
| | TaqMan® probe | /56-FAM/TGTGCACTG/ZEN/AGTAGCAG/3IABkFQ/ (SEQ ID NO: 34) |

SUPPLEMENTARY TABLE S2-continued

Sequences of adapters and primers for 5'-Db-PCR

| Target | Primer/adapter | Sequence (5'-3') |
| --- | --- | --- |
| miR-26a | 5'-Db-adapter | CTTGAACTCAGTGCGTGGGAGGGTGTGTGGTCTTGCTTGGTGTGCACTGrArG<br>(SEQ ID NO: 35) |
| | RT primer | CAGCCTATCCTGGATTA<br>(SEQ ID NO: 36) |
| | Reverse primer | CAGCCTATCCTGGATTA<br>(SEQ ID NO: 36) |
| | Forward primer | GAGGGTGTGTGGTCTT<br>(SEQ ID NO: 14) |
| | TaqMan® probe | /56-FAM/TGTGCACTG/ZEN/AGTTCAAG/3IABkFQ/<br>(SEQ ID NO: 37) |
| miR-26a-[5' + A] | 5'-Db-adapter | TTGAATCTCAGTGCGTGGGAGGGTGTGTGGTCTTGCTTGGTGTGCACTGrArG<br>(SEQ ID NO: 38) |
| | RT primer | CAGCCTATCCTGGATTA<br>(SEQ ID NO: 36) |
| | Reverse primer | CAGCCTATCCTGGATTA<br>(SEQ ID NO: 36) |
| | Forward primer | GAGGGTGTGTGGTCTT<br>(SEQ ID NO: 14) |
| | TaqMan® probe | /56-FAM/TGTGCACTG/ZEN/AGATTCAA/3IABkFQ/<br>(SEQ ID NO: 62) |

A, G, C, and T designate DNA, whereas rA and rG designate RNA.

SUPPLEMENTARY TABLE S3

Sequences of adaptors and primers for Db-PCR

| Target | Primer/Adapter | Sequence (5'-3') |
| --- | --- | --- |
| miR-16 | 5'-Dbs-adapter-6 | CTGCTACGTCG/idSp/TGGAGTGTGTGCTTTGArCrG<br>(SEQ ID NO: 39) |
| | 5'-Dbs-adapter-12 | TACGTGCTGCTACGTCG/idSp/TGGAGTGTGTGCTTTGArCrG<br>(SEQ ID NO: 40) |
| | 5'-Dbs-adapter-16 | TATTTACGTGCTGCTACGTCG/idSp/TGGAGTGTGTGCTTTGArCrG<br>(SEQ ID NO: 41) |
| | 3'-Db-adapter | /5Phos/CTCAGTGCAGGGTCCGAGGTATTCGCACTGAGCGCCAA<br>(SEQ ID NO: 42) |
| | RT primer | CTCAGTGCGAATACCTCGGACCCT<br>(SEQ ID NO: 12) |
| | Reverse primer | CGAATACCTCGGACC<br>(SEQ ID NO: 13) |
| | Forward primer | TGGAGTGTGTGCTTTGACGTAGC<br>(SEQ ID NO: 43) |
| | TaqMan® probe | /56-FAM/AAATATTGG/ZEN/CGCTCAGTGCA/3IABkFQ/<br>(SEQ ID NO: 44) |
| miR-21 | 5'-Dbs-adapter | TCAGTCTGATAAGCTACGTCG/idSp/TGGAGTGTGTGCTTTGArCrG<br>(SEQ ID NO: 45) |
| | 3'-Db-adapter | /5Phos/CTCAGTGCAGGGTCCGAGGTATTCGCACTGAGTCAACA<br>(SEQ ID NO: 46) |
| | RT primer | CTCAGTGCGAATACCTCGGACCCT<br>(SEQ ID NO: 12) |
| | Reverse primer | CGAATACCTCGGACC<br>(SEQ ID NO: 13) |
| | Forward primer | TGGAGTGTGTGCTTTGACGTAGC<br>(SEQ ID NO: 43) |
| | TaqMan® probe | /56-FAM/AGACTGATG/ZEN/TTGCTCAGTGCA/3IABkFQ/<br>(SEQ ID NO: 47) |
| piR-2 | 5'-Dbs-adapter | AAATTCTCATGCTTTTCGTCG/idSp/TGGAGTGTGTGCTTTGArCrG<br>(SEQ ID NO: 48) |
| | 3'-Db-adapter | /5Phos/CTCAGTGCAGGGTCCGAGGTATTCGCACTGAGCCGCAG<br>(SEQ ID NO: 49) |
| | RT primer | CTCAGTGCGAATACCTCGGACCCT<br>(SEQ ID NO: 12) |
| | Reverse primer | CGAATACCTCGGACC<br>(SEQ ID NO: 13) |
| | Forward primer | TGGAGTGTGTGCTTTGACGAAAAG<br>(SEQ ID NO: 50) |

SUPPLEMENTARY TABLE S3-continued

Sequences of adaptors and primers for Db-PCR

| Target | Primer/Adapter | Sequence (5'-3') |
|---|---|---|
| | TaqMan® probe | /56-FAM/CTGCGGTC/ZEN/AGTGCA/3IABkFQ/ (SEQ ID NO: 51) |
| piR-2-[3' + ACCA] | 5'-Dbs-adapter | AAATTCTCATGCTTTTCGTCG/idSp/TGGAGTGTGTGCTTTGArCrG (SEQ ID NO: 52) |
| | 3'-Db-adapter | /5Phos/CTCAGTGCAGGGTCCGAGGTATTCGCACTGAGTGGTCC (SEQ ID NO: 53) |
| | RT primer | CTCAGTGCGAATACCTCGGACCCT (SEQ ID NO: 12) |
| | Reverse primer | CGAATACCTCGGACC (SEQ ID NO: 13) |
| | Forward primer | TGGAGTGTGTGCTTTGACGAAAAG (SEQ ID NO: 50) |
| | TaqMan® probe | /56-FAM/CGGACCACT/ZEN/CAGTGCAG/3IABkFQ/ (SEQ ID NO: 31) |

All publications cited are incorporated herein in their entirety.

What is claimed is:

1. A method to quantify specific small RNA variants comprising:
   a) creating the following adapters and primers: (i) a 5'-Dbs-adapter wherein the nucleotide sequence of the 5'-Dbs-adapter is SEQ ID NO: 3, wherein SEQ ID NO: 3 includes a stem-loop structure with the stem formed between nucleotides 17-20 and nucleotides 37-40, and wherein the 5'-terminal 16 nucleotides of SEQ ID NO: 3 are complementary to a 5'-terminal sequence of target RNAs; (ii) a 3'-Db-adapter that has a stem-loop structure and whose protruding 3'-terminal six nucleotides are complementary to a 3'-terminal sequence of the target RNAs; (iii) an RT primer; (iv) a reverse primer; (v) a forward primer; and (vi) a probe targeting the boundary of a target RNA and the 3'-Db-adapter, wherein the probe contains a 5' fluorophore and a 3' quencher;
b) hybridizing the 5'-Dbs-adapter to the 5'-end of the target RNAs, wherein the loop region of the 5'-Dbs-adapter contains a base-lacking spacer which will terminate reverse transcription;
c) hybridizing the 3'-Db-adapter to the 3'-end of the target RNAs;
d) ligating both adapters with the target RNAs by Rnl2 ligation to form "dumbbell-like" structure ligation products; and
e) amplifying and quantifying the ligation products by RT-PCR assay using a DNA polymerase with 5' exonuclease activity, wherein the probe is designed to target the boundary of the 3'-Db-adapter and target RNAs to exclusively quantify ligated target RNAs.

2. The method of claim 1, wherein the nucleotide sequence of the probe hybridized at the boundary of the 3'-Db-adapter and target RNA is SEQ ID NO: 44.

3. The method of claim 1, wherein the nucleotide sequence of the 5'-Dbs-adapter is SEQ ID NO: 41.

4. The method of claim 1, wherein the nucleotide sequence of the 3'-Db-adapter is SEQ ID NO: 1.

5. The method of claim 1, wherein the nucleotide sequence of the RT primer is SEQ ID NO: 12.

6. The method of claim 1, wherein the nucleotide sequence of the reverse primer is SEQ ID NO: 13.

7. The method of claim 1, wherein the nucleotide sequence of the forward primer is SEQ ID NO: 15.

8. A method to quantify specific small RNA variants with single nucleotide resolution at a 5'-terminal sequence comprising:
a) creating the following adapters and primers: (i) a 5'-Db-adapter, wherein the nucleotide sequence of the 5'-Db-adapter is SEQ ID NO: 2, wherein SEQ ID NO: 2 includes a stem-loop structure with the stem formed between nucleotides 7-15 and nucleotides 43-51, and wherein the 5'-terminal six nucleotides of SEQ ID NO: 2 are complementary to 5'-terminal sequences of target RNAs; (ii) an RT/R primer which is complementary to a 3'-terminal sequence of the target RNAs; (iii) a forward primer; and (iv) a probe targeting the boundary of a target RNA and the 5'-Db-adapter, wherein the probe contains a 5' fluorophore and a 3' quencher;
b) hybridizing the 5'-Db-adapter to the 5'-end of target RNAs;
c) ligating the 5'-Db-adapter with target RNAs by Rnl2 ligation to form ligation products; and
d) amplifying and quantifying the ligation products by RT-PCR PCR assay using a DNA polymerase with 5' exonuclease activity, wherein the probe is designed to target the boundary of the 5'-Db-adapter and target RNAs to exclusively quantify ligated target RNAs.

9. A method to quantify specific small RNA variants with single nucleotide resolution at a 3'-terminal sequence comprising:
a) creating the following: (i) a 3'-Db-adapter, wherein the nucleotide sequence of the 3'-Db-adapter is SEQ ID NO: 1, wherein the SEQ ID NO: 1 includes a stem-loop structure with the stem formed between nucleotides 1-8 and 25-32, and wherein the six 3' nucleotides of SEQ ID NO: 1 are complementary to a 3'-terminal sequence of target RNAs; (ii) an RT primer; (iii) a reverse primer; (iv) a forward primer which is complementary to a 5'-terminal sequence of target RNAs; and (v) a probe targeting the boundary of the target RNAs and the 3'-Db-adapter, wherein the probe contains a 5' fluorophore and a 3' quencher;
b) hybridizing the 3'-Db-adapter to the 3'-end of the target RNAs;
c) ligating the 3'-Db-adapter with the target RNAs by Rnl2 ligation to form ligation products; and
d) amplifying and quantifying the ligation products by RT-PCR PCR assay using a DNA polymerase with 5' exonuclease activity, wherein the probe is designed to target the boundary of the 3'-Db-adapter and target RNAs to exclusively quantify ligated target RNAs.

10. The method of claim 9, wherein the RT primer is SEQ ID NO: 12.

11. The method of claim 9, wherein the reverse primer is SEQ ID NO: 13.

* * * * *